US010507034B2

(12) United States Patent
Timm

(10) Patent No.: US 10,507,034 B2
(45) Date of Patent: Dec. 17, 2019

(54) SURGICAL INSTRUMENT WITH MOTORIZED ARTICULATION DRIVE IN SHAFT ROTATION KNOB

(71) Applicant: Ethicon Endo-Surgery, LLC, Guaynabo, PR (US)

(72) Inventor: Richard W. Timm, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 395 days.

(21) Appl. No.: 15/089,733

(22) Filed: Apr. 4, 2016

(65) Prior Publication Data
US 2017/0281218 A1 Oct. 5, 2017

(51) Int. Cl.
*A61B 17/32* (2006.01)
*A61B 17/29* (2006.01)
*A61B 17/00* (2006.01)

(52) U.S. Cl.
CPC .. *A61B 17/320092* (2013.01); *A61B 17/2909* (2013.01); *A61B 2017/00309* (2013.01); *A61B 2017/00327* (2013.01); *A61B 2017/00398* (2013.01); *A61B 2017/293* (2013.01); *A61B 2017/2905* (2013.01); *A61B 2017/2913* (2013.01); *A61B 2017/2916* (2013.01); *A61B 2017/2923* (2013.01); *A61B 2017/2927* (2013.01); *A61B 2017/2929* (2013.01)

(58) Field of Classification Search
CPC ...... A61B 17/320092; A61B 17/00234; A61B 2017/00309; A61B 2017/00314; A61B 2017/00327; A61B 2017/00398; A61B 2017/2905; A61B 2017/2913; A61B 2017/2916; A61B 2017/2923; A61B 2017/2927; A61B 2017/2929; A61B 2017/293; A61B 17/2909
See application file for complete search history.

(56) References Cited

U.S. PATENT DOCUMENTS

| 5,322,055 A | 6/1994 | Davison et al. |
| 5,873,873 A | 2/1999 | Smith et al. |
| 5,897,523 A | 4/1999 | Wright et al. |
| 5,980,510 A | 11/1999 | Tsonton et al. |

(Continued)

FOREIGN PATENT DOCUMENTS

EP 2 982 318 A1 2/2016

OTHER PUBLICATIONS

U.S. Appl. No. 14/258,179, filed Apr. 22, 2014.
(Continued)

*Primary Examiner* — Jing Rui Ou
(74) *Attorney, Agent, or Firm* — Frost Brown Todd LLC

(57) ABSTRACT

An apparatus includes a body assembly, a shaft defining a longitudinal axis extending from the body assembly, an acoustic waveguide having a flexible portion, and an articulation section coupled with the shaft. A portion of the articulation section encompasses the flexible portion of the waveguide. The articulation section has a first member and a second member translatable relative to the first member. An end effector has an ultrasonic blade that is in communication with the waveguide. An articulating control assembly has a motor. The motor is operable to translate the first and second members to thereby deflect the end effector away from the longitudinal axis at the articulation section.

13 Claims, 18 Drawing Sheets

(56) References Cited

U.S. PATENT DOCUMENTS

| | | | |
|---|---|---|---|
| 5,989,264 A | 11/1999 | Wright | |
| 6,063,098 A | 5/2000 | Houser et al. | |
| 6,090,120 A | 7/2000 | Wright et al. | |
| 6,325,811 B1 | 12/2001 | Messerly | |
| 6,454,782 B1 | 9/2002 | Schwemberger | |
| 6,589,200 B1 | 7/2003 | Schwemberger et al. | |
| 6,752,815 B2 | 6/2004 | Beaupre | |
| 6,773,444 B2 | 8/2004 | Messerly | |
| 6,783,524 B2 | 8/2004 | Anderson et al. | |
| 7,135,030 B2 | 11/2006 | Schwemberger et al. | |
| 7,431,188 B1 * | 10/2008 | Marczyk | A61B 17/072 227/175.1 |
| 7,621,930 B2 | 11/2009 | Houser | |
| 8,461,744 B2 | 6/2013 | Wiener et al. | |
| 8,591,536 B2 | 11/2013 | Robertson | |
| 8,623,027 B2 | 1/2014 | Price et al. | |
| 8,663,220 B2 | 3/2014 | Wiener et al. | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 9,737,300 B2 | 8/2017 | Parihar et al. | |
| 2002/0120252 A1 * | 8/2002 | Brock | A61B 17/0469 606/1 |
| 2002/0143319 A1 * | 10/2002 | Brock | A61B 5/0086 606/1 |
| 2003/0036748 A1 * | 2/2003 | Cooper | A61B 17/00234 606/1 |
| 2003/0208186 A1 * | 11/2003 | Moreyra | A61B 34/71 606/1 |
| 2005/0021065 A1 * | 1/2005 | Yamada | A61B 17/32002 606/169 |
| 2005/0096694 A1 * | 5/2005 | Lee | A61B 17/00234 606/205 |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2008/0223903 A1 * | 9/2008 | Marczyk | A61B 17/072 227/175.1 |
| 2009/0090763 A1 * | 4/2009 | Zemlok | A61B 17/07207 227/175.2 |
| 2010/0249497 A1 * | 9/2010 | Peine | A61B 1/005 600/104 |
| 2012/0078243 A1 * | 3/2012 | Worrell | A61B 17/07207 606/33 |
| 2012/0078247 A1 | 3/2012 | Worrell et al. | |
| 2012/0112687 A1 | 5/2012 | Houser et al. | |
| 2012/0116265 A1 | 5/2012 | Houser et al. | |
| 2013/0023868 A1 * | 1/2013 | Worrell | A61B 17/07207 606/33 |
| 2013/0030428 A1 * | 1/2013 | Worrell | A61B 5/0205 606/33 |
| 2013/0289592 A1 | 10/2013 | Stulen et al. | |
| 2013/0324998 A1 * | 12/2013 | Kimball | A61B 17/320068 606/41 |
| 2014/0005701 A1 | 1/2014 | Olson et al. | |
| 2014/0005702 A1 * | 1/2014 | Timm | A61B 17/29 606/169 |
| 2014/0005703 A1 | 1/2014 | Stulen et al. | |
| 2015/0053744 A1 * | 2/2015 | Swayze | A61B 17/072 227/176.1 |
| 2015/0080924 A1 | 3/2015 | Stulen et al. | |
| 2015/0141981 A1 | 5/2015 | Price et al. | |
| 2015/0320437 A1 | 11/2015 | Worrell et al. | |
| 2016/0022299 A1 * | 1/2016 | Sakaguchi | A61B 17/29 606/34 |

OTHER PUBLICATIONS

U.S. Appl. No. 14/688,458, filed Apr. 16, 2015.
U.S. Appl. No. 61/410,603, filed Nov. 5, 2010.
International Search Report and Written Opinion dated Jul. 11, 2017 for Application No. PCT/US2017/025940, 13 pgs.

* cited by examiner

SURGICAL INSTRUMENT WITH MOTORIZED ARTICULATION DRIVE IN SHAFT ROTATION KNOB

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pub. No. 2009/0105750, entitled "Ergonomic Surgical Instruments," published Apr. 23, 2009, the disclosure of which is incorporated by reference herein; U.S. Pub. No. 2010/0069940, entitled "Ultrasonic Device for Fingertip Control," published Mar. 18, 2010, the disclosure of which is incorporated by reference herein; and U.S. Pub. No. 2011/0015660, entitled "Rotating Transducer Mount for Ultrasonic Surgical Instruments," published Jan. 20, 2011, the disclosure of which is incorporated by reference herein; and U.S. Pub. No. 2012/0029546, entitled "Ultrasonic Surgical Instrument Blades," published Feb. 2, 2012, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section and/or a bendable ultrasonic waveguide. Examples of such ultrasonic surgical instruments are disclosed in U.S. Pat. No. 5,897,523, entitled "Articulating Ultrasonic Surgical Instrument," issued Apr. 27, 1999, the disclosure of which is incorporated by reference herein; U.S. Pat. No. 5,989,264, entitled "Ultrasonic Polyp Snare," issued Nov. 23, 1999, the disclosure of which is incorporated by reference herein; U.S. Pat. No. 6,063,098, entitled "Articulable Ultrasonic Surgical Apparatus," issued May 16, 2000, the disclosure of which is incorporated by reference herein; U.S. Pat. No. 6,090,120, entitled "Articulating Ultrasonic Surgical Instrument," issued Jul. 18, 2000, the disclosure of which is incorporated by reference herein; U.S. Pat. No. 6,454,782, entitled "Actuation Mechanism for Surgical Instruments," issued Sep. 24, 2002, the disclosure of which is incorporated by reference herein; U.S. Pat. No. 6,589,200, entitled "Articulating Ultrasonic Surgical Shears," issued Jul. 8, 2003, the disclosure of which is incorporated by reference herein; U.S. Pat. No. 6,752,815, entitled "Method and Waveguides for Changing the Direction of Longitudinal Vibrations," issued Jun. 22, 2004, the disclosure of which is incorporated by reference herein; U.S. Pat. No. 7,135,030, entitled "Articulating Ultrasonic Surgical Shears," issued Nov. 14, 2006; U.S. Pat. No. 7,621,930, entitled "Ultrasound Medical Instrument Having a Medical Ultrasonic Blade," issued Nov. 24, 2009, the disclosure of which is incorporated by reference herein; U.S. Pub. No. 2014/0005701, published Jan. 2, 2014, entitled "Surgical Instruments with Articulating Shafts," the disclosure of which is incorporated by reference herein; U.S. Pub. No. 2014/005703, entitled "Surgical Instruments with Articulating Shafts," published Jan. 2, 2014, the disclosure of which is incorporated by reference herein; U.S. Pub. No. 2014/0114334, entitled "Flexible Harmonic Waveguides/Blades for Surgical Instruments," published Apr. 24, 2014, the disclosure of which is incorporated by reference herein; U.S. Pub. No. 2015/0080924, entitled "Articulation Features for Ultrasonic Surgical Instrument," published Mar. 19, 2015, the disclosure of which is incorporated by reference herein; and U.S. patent application Ser. No. 14/258,179, entitled "Ultrasonic Surgical Device with Articulating End Effector," filed Apr. 22, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
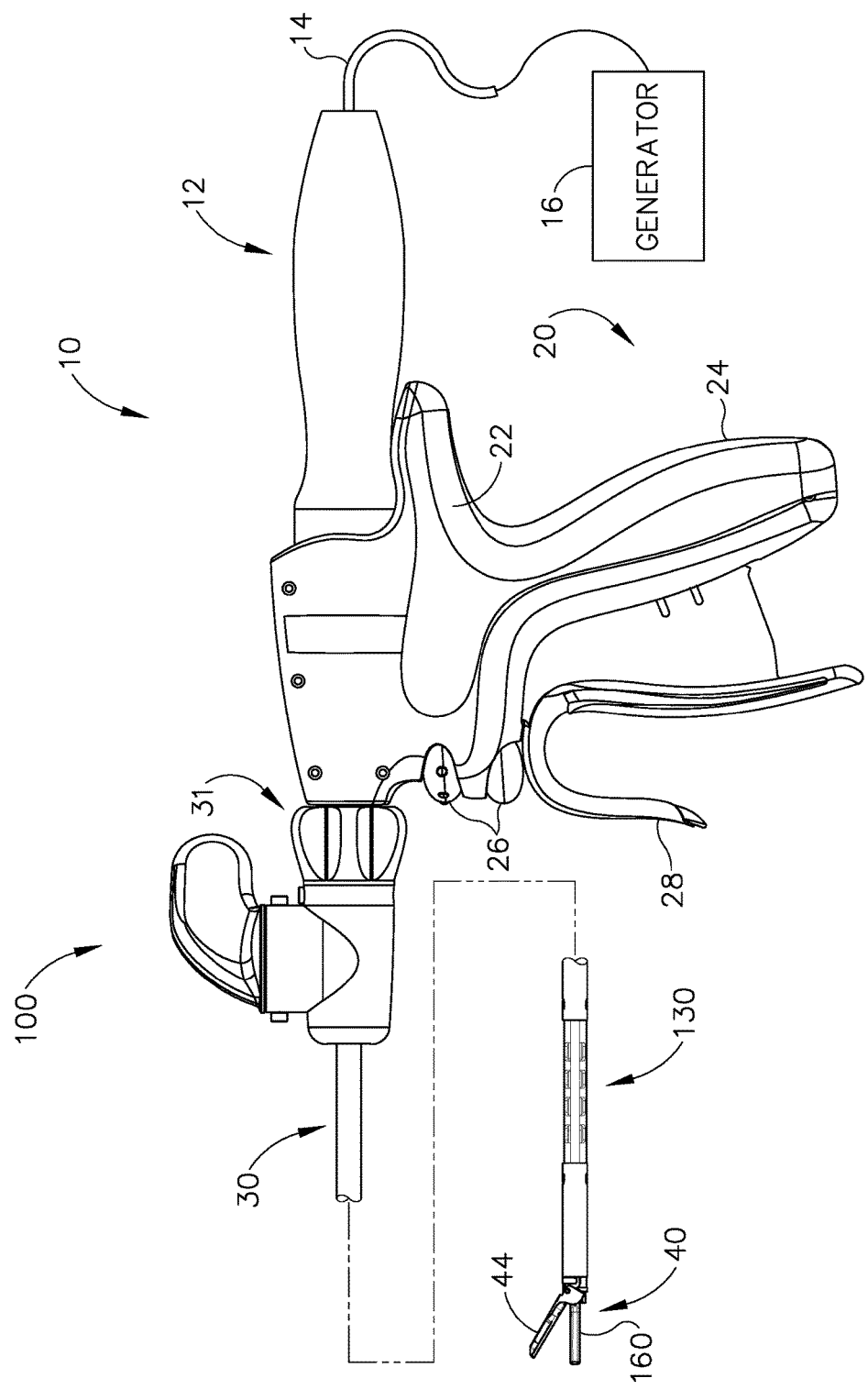
FIG. 1 depicts a side elevational view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIG. 1 shows an exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously.

Instrument (10) of the present example comprises a handle assembly (20), a shaft assembly (30), and an end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. End effector (40) includes an ultrasonic blade (160) and a pivoting clamp arm (44). Clamp arm (44) is coupled with trigger (28) such that clamp arm (44) is pivotable toward ultrasonic blade (160) in response to pivoting of trigger (28) toward pistol grip (24); and such that clamp arm (44) is pivotable away from ultrasonic blade (160) in response to pivoting of trigger (28) away from pistol grip (24). Various suitable ways in which clamp arm (44) may be coupled with trigger (28) will be apparent to those of ordinary skill in the art in view of the teachings herein. In some versions, one or more resilient members are used to bias clamp arm (44) and/or trigger (28) to the open position shown in FIG. 1.

An ultrasonic transducer assembly (12) extends proximally from body (22) of handle assembly (20). Transducer assembly (12) is coupled with a generator (16) via a cable (14), such that transducer assembly (12) receives electrical power from generator (16). Piezoelectric elements in transducer assembly (12) convert that electrical power into ultrasonic vibrations. Generator (16) may include a power source and control module that is configured to provide a power profile to transducer assembly (12) that is particularly suited for the generation of ultrasonic vibrations through transducer assembly (12). By way of example only, generator (16) may comprise a GEN04 or GEN11 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

A. Exemplary End Effector and Acoustic Drivetrain

Figure 2:
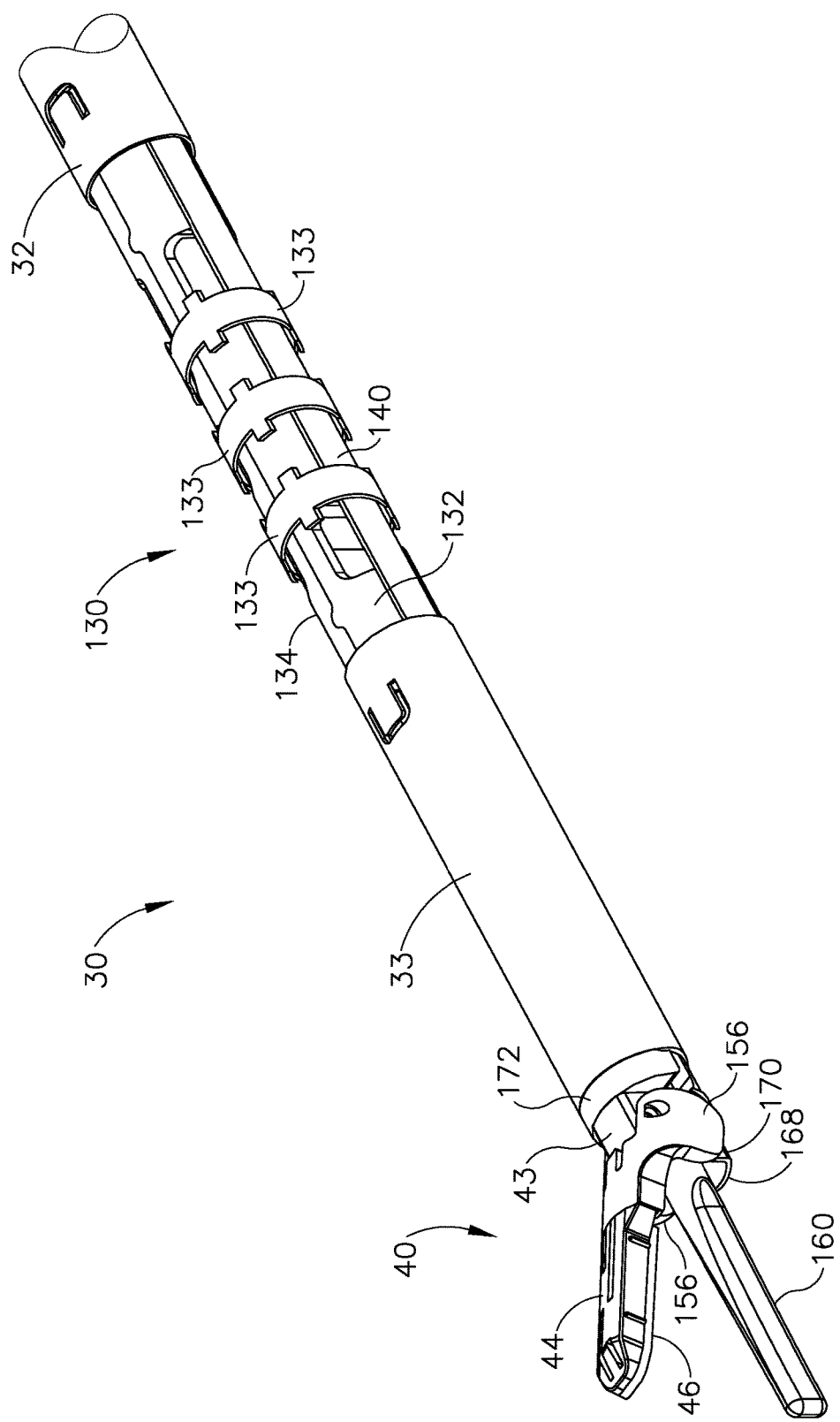
FIG. 2 depicts a perspective view of an articulation section of a shaft assembly and an end effector of the surgical instrument of FIG. 1.
Figure 3:
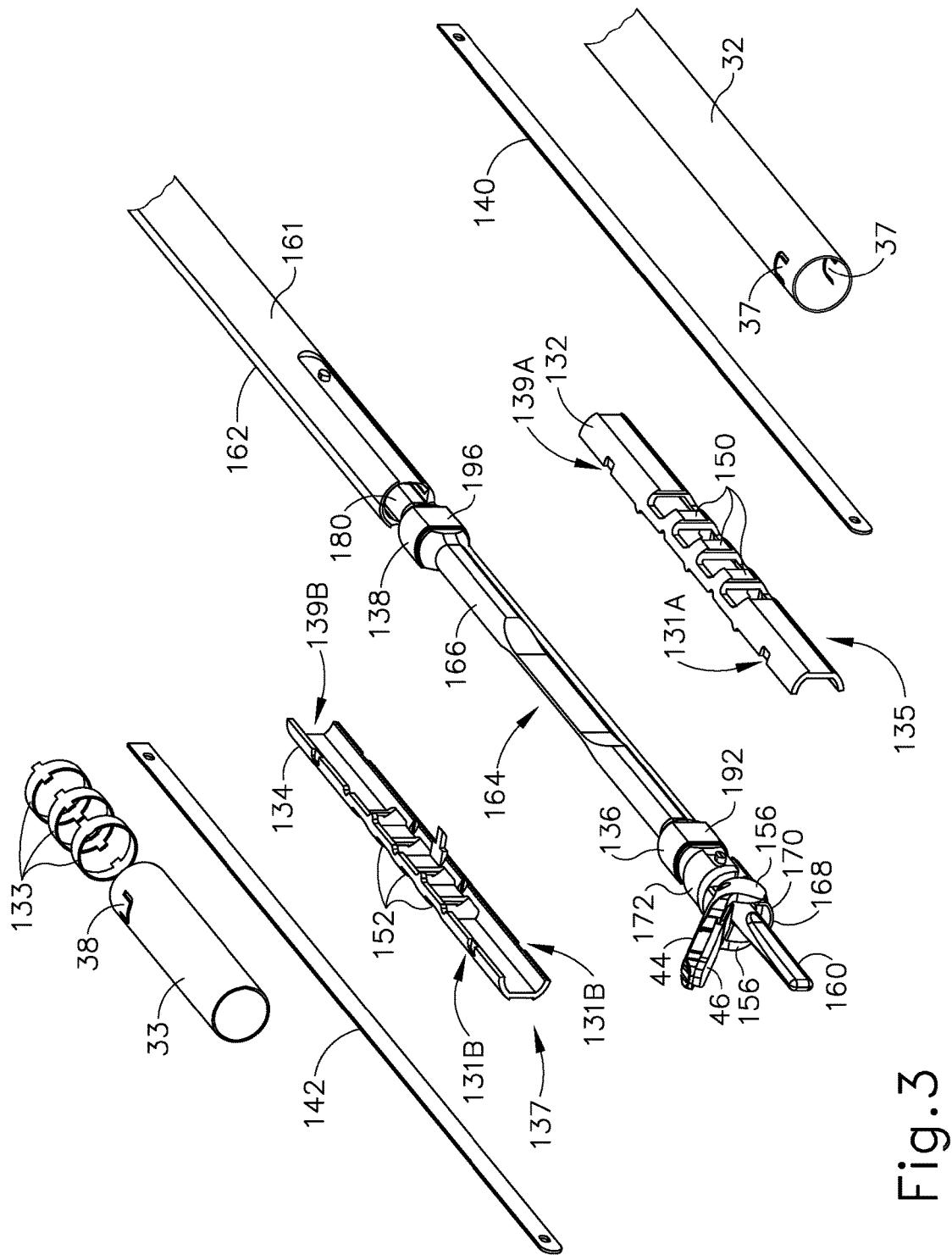
FIG. 3 depicts an exploded perspective view of an articulation section of the shaft assembly of FIG. 2.
Figure 4:
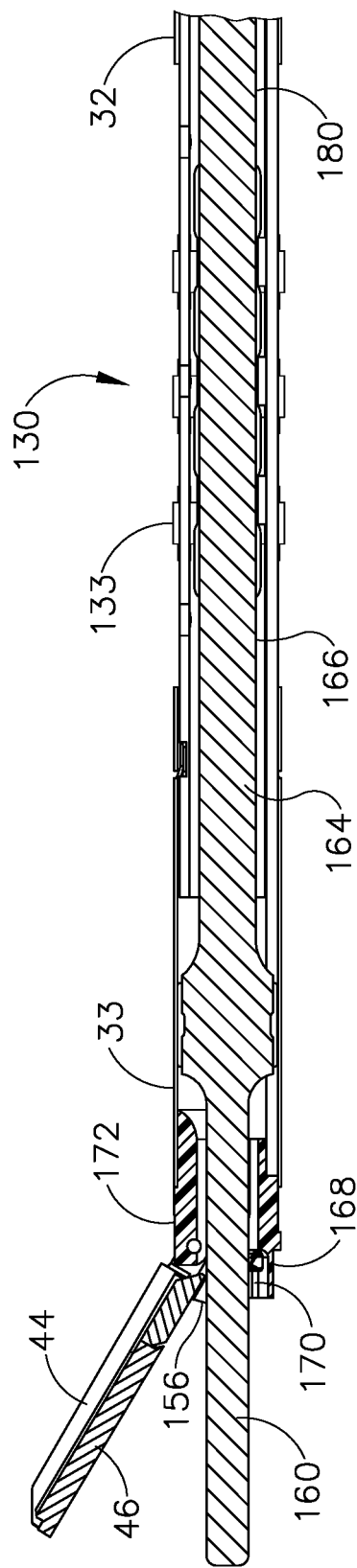
FIG. 4 depicts a cross-sectional side view of the shaft assembly and end effector of FIG. 2.

As best seen in FIGS. 2-4, end effector (40) of the present example comprises clamp arm (44) and ultrasonic blade (160). Clamp arm (44) includes a clamp pad (46) that is secured to the underside of clamp arm (44), facing blade (160). Clamp pad (46) may comprise polytetrafluoroethylene (PTFE) and/or any other suitable material(s). Clamp arm (44) is pivotally secured to a distally projecting tongue (43) of an upper distal shaft element (172), which is fixedly secured within a distal portion of a distal outer sheath (33). Clamp arm (44) is operable to selectively pivot toward and away from blade (160) to selectively clamp tissue between clamp arm (44) and blade (160). A pair of arms (156) extend transversely from clamp arm (44) and are pivotally secured to a lower distal shaft element (170), which is slidably disposed within the distal portion of distal outer sheath (33).

In some examples a cable (not shown) may be secured to lower distal shaft element (170). Such a cable may be operable to translate longitudinally relative to an articulation section (130) of shaft assembly (30) to selectively pivot clamp arm (44) toward and away from blade (160). In further examples, the cable is coupled with trigger (28) such that the cable translates proximally in response to pivoting of trigger (28) toward pistol grip (24), and such that clamp arm (44) thereby pivots toward blade (160) in response to pivoting of trigger (28) toward pistol grip (24). In addition, the cable may translate distally in response to pivoting of trigger (28) away from pistol grip (24), such that clamp arm (44) pivots away from blade (160) in response to pivoting of trigger (28) away from pistol grip (24).

Blade (160) of the present example is operable to vibrate at ultrasonic frequencies in order to effectively cut through and seal tissue, particularly when the tissue is being compressed between clamp pad (46) and blade (160). Blade (160) is positioned at the distal end of an acoustic drivetrain. This acoustic drivetrain includes transducer assembly (12) and an acoustic waveguide (180). Acoustic waveguide (180) comprises a flexible portion (166). As noted above, transducer assembly (12) is operable to convert electrical power into ultrasonic vibrations, which are then transmitted along waveguide (180), including flexible portion (166) of waveguide (180) to blade (160) in accordance with known configurations and techniques. By way of example only, this portion of the acoustic drivetrain may be configured in accordance with various teachings of various references that are cited herein.

As best seen in FIG. 3, flexible portion (166) of waveguide (180) includes a distal flange (136), a proximal flange (138), and a narrowed section (164) located between flanges (136, 138). In the present example, flanges (136, 138) are located at positions corresponding to nodes associated with resonant ultrasonic vibrations communicated through flexible portion (166) of waveguide (180) (i.e., at locations where the vibrational amplitude is minimal). Narrowed section (164) is configured to allow flexible portion (166) of waveguide (180) to flex without significantly affecting the ability of flexible portion (166) of waveguide (180) to transmit ultrasonic vibrations. By way of example only, narrowed section (164) may be configured in accordance with one or more teachings of U.S. Pub. No. 2014/0005701 and/or U.S. Pub. No. 2014/0114334, the disclosures of which are incorporated by reference herein. It should be understood that waveguide (180) may be configured to amplify mechanical vibrations transmitted through waveguide (180). Furthermore, waveguide (180) may include features operable to control the gain of the longitudinal vibrations along waveguide (180) and/or features to tune waveguide (180) to the resonant frequency of the system. Various suitable ways in which waveguide (180) may be mechanically and acoustically coupled with transducer assembly (12) will be apparent to those of ordinary skill in the art in view of the teachings herein.

Those of ordinary skill in the art will understand that, as a matter of physics, the distal end of blade (24) is located at a position corresponding to an anti-node associated with resonant ultrasonic vibrations communicated through waveguide (28) (i.e., at an acoustic anti-node). When transducer assembly (12) is energized, the distal end of blade (160) is configured to move longitudinally in the range of, for example, approximately 10 to 500 microns peak-to-peak, and in some instances in the range of about 20 to about 200 microns at a predetermined vibratory frequency $f_0$ of, for example, 55.5 kHz. When transducer assembly (12) of the present example is activated, these mechanical oscillations are transmitted through waveguide (180) to reach blade (160), thereby providing oscillation of blade (160) at the resonant ultrasonic frequency. Thus, when tissue is secured between blade (160) and clamp pad (46), the ultrasonic oscillation of blade (160) may simultaneously sever the tissue and denature the proteins in adjacent tissue cells, thereby providing a coagulative effect with relatively little thermal spread.

In some versions, end effector (40) is operable to apply radiofrequency (RF) electrosurgical energy to tissue in addition to applying ultrasonic energy to tissue. By way of example only, end effector (40) may be configured and operable in accordance with at least some of the teachings of U.S. Pub. No. 2015/0141981, entitled "Ultrasonic Surgical Instrument with Electrosurgical Feature," published May 21, 2015, the disclosure of which is incorporated by reference herein; and/or U.S. Pat. No. 8,663,220, entitled "Ultrasonic Electrosurgical Instruments," issued Mar. 4, 2014, the disclosure of which is incorporated by reference herein.

Other suitable configurations for an acoustic transmission assembly and transducer assembly (12) will be apparent to one of ordinary skill in the art in view of the teachings herein. Similarly, other suitable configurations for end effector (40) will be apparent to those of ordinary skill in the art in view of the teachings herein.

B. Exemplary Shaft Assembly and Articulation Section

Shaft assembly (30) of the present example extends distally from handle assembly (20). As shown in FIGS. 2-6B, shaft assembly (30) includes distal outer sheath (33) and a proximal outer sheath (32) that enclose clamp arm (44) drive features and the above-described acoustic transmission features. Shaft assembly (30) further includes an articulation section (130), which is located at a distal portion of shaft assembly (30), with end effector (40) being located distal to articulation section (130). As shown in FIG. 1, a knob (31) is secured to a proximal portion of proximal outer sheath (32). Knob (31) is rotatable relative to body (22), such that shaft assembly (30) is rotatable about the longitudinal axis defined by outer sheath (32), relative to handle assembly (20). Such rotation may provide rotation of end effector (40), articulation section (130), and shaft assembly (30) unitarily. Of course, rotatable features may simply be omitted if desired.

Articulation section (130) is operable to selectively position end effector (40) at various lateral deflection angles relative to a longitudinal axis defined by outer sheath (32). Articulation section (130) may take a variety of forms. By way of example only, articulation section (130) may be configured in accordance with one or more teachings of U.S. Pub. No. 2012/0078247, the disclosure of which is incorporated by reference herein. As another merely illustrative example, articulation section (130) may be configured in accordance with one or more teachings of U.S. Pub. No. 2014/0005701 and/or U.S. Pub. No. 2014/0114334, the disclosures of which are incorporated by reference herein. Various other suitable forms that articulation section (130) may take will be apparent to those of ordinary skill in the art in view of the teachings herein.

As best seen in FIGS. 2-6B articulation section (130) of this example comprises a set of three outer rings (133) and a pair of ribbed body portions (132, 134), with a pair of articulation bands (140, 142) extending along respective channels (135, 137) defined between interior surfaces of outer rings (133) and exterior surfaces of ribbed body portions (132, 134). Ribbed body portions (132, 134) are longitudinally positioned between flanges (136, 138) of flexible portion (166) of waveguide (180). In some versions, ribbed body portions (132, 134) snap together about flexible portion (166) of waveguide (180). Ribbed body portions (132, 134) are configured to flex with flexible portion (166) of waveguide (180) when articulation section (130) bends to achieve an articulated state.

FIG. 3 shows ribbed body portions (132, 134) in greater detail. In the present example, ribbed body portions (132, 134) are formed of a flexible plastic material, though it should be understood that any other suitable material may be used. Ribbed body portion (132) comprises a set of three ribs (150) that are configured to promote lateral flexing of ribbed body portion (132). Of course, any other suitable number of ribs (150) may be provided. Ribbed body portion (132) also defines a channel (135) that is configured to receive articulation band (140) while allowing articulation band (140) to slide relative to ribbed body portion (132). Similarly, ribbed body portion (134) comprises a set of three ribs (152) that are configured to promote lateral flexing of ribbed body portion (134). Of course, any other suitable number of ribs (152) may be provided. Ribbed body portion (134) also defines a channel (137) that is configured to receive articulation band (142) while allowing articulation band (142) to slide relative to ribbed body portion (137).

Figure 5:
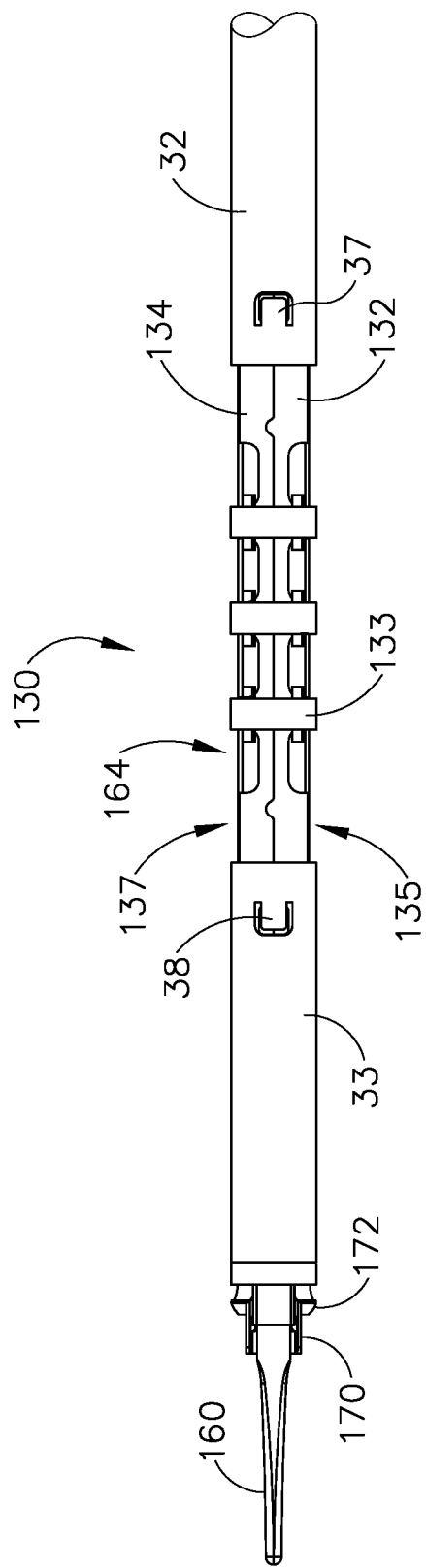
FIG. 5 depicts a top plan view of the shaft assembly and end effector of FIG. 2.

As best seen in FIG. 5, ribbed body portions (132, 134) are laterally interposed between articulation bands (140, 142) and flexible portion (166) of waveguide (180). Ribbed body portions (132, 134) mate with each other such that they together define an internal passage sized to accommodate flexible portion (166) of waveguide (180) without contacting waveguide (180). In addition, when ribbed body portions (132, 134) are coupled together, a pair of complementary distal notches (131A, 131B) formed in ribbed body portions (132, 134) align to receive a pair of inwardly projecting resilient tabs (38) of distal outer sheath (33). This engagement between tabs (38) and notches (131A, 131B) longitudinally secures ribbed body portions (132, 134) relative to distal outer sheath (33). Similarly, when ribbed body portions (132, 134) are coupled together, a pair of complementary proximal notches (139A, 139B) formed in ribbed body portions (132, 134) align to receive a pair of inwardly projecting resilient tabs (37) of proximal outer sheath (32). This engagement between tabs (37) and notches (139A, 139B) longitudinally secures ribbed body portions (132, 134) relative to proximal outer sheath (32). Of course, any other suitable kinds of features may be used to couple ribbed body portions (132, 134) with proximal outer sheath (32) and/or distal outer sheath (33).

Figure 6A:
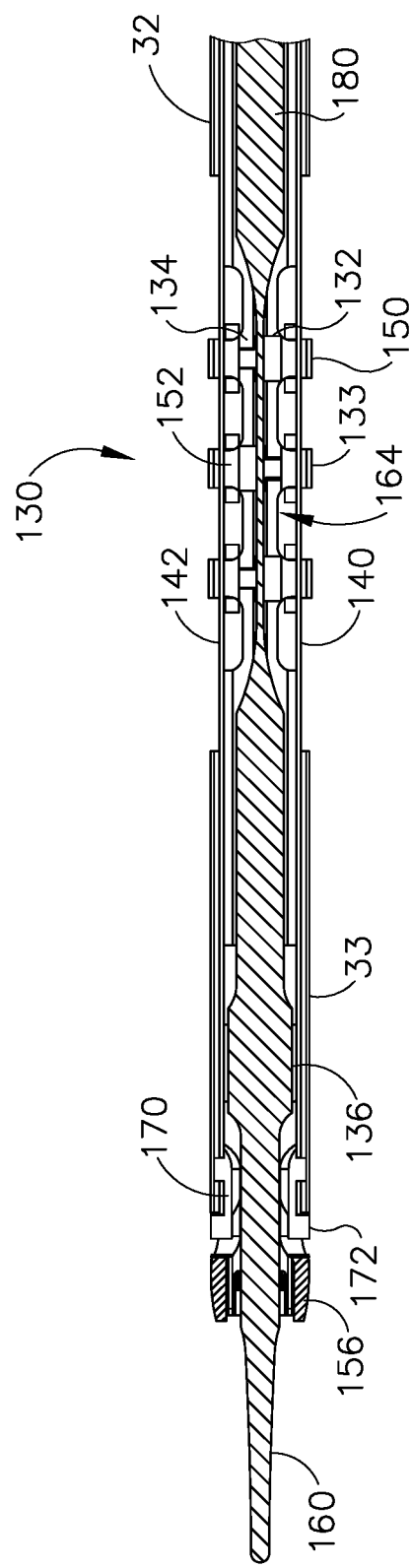
FIG. 6A depicts a cross-sectional top view of the shaft assembly and end effector of FIG. 2 in a straight configuration.
Figure 6B:
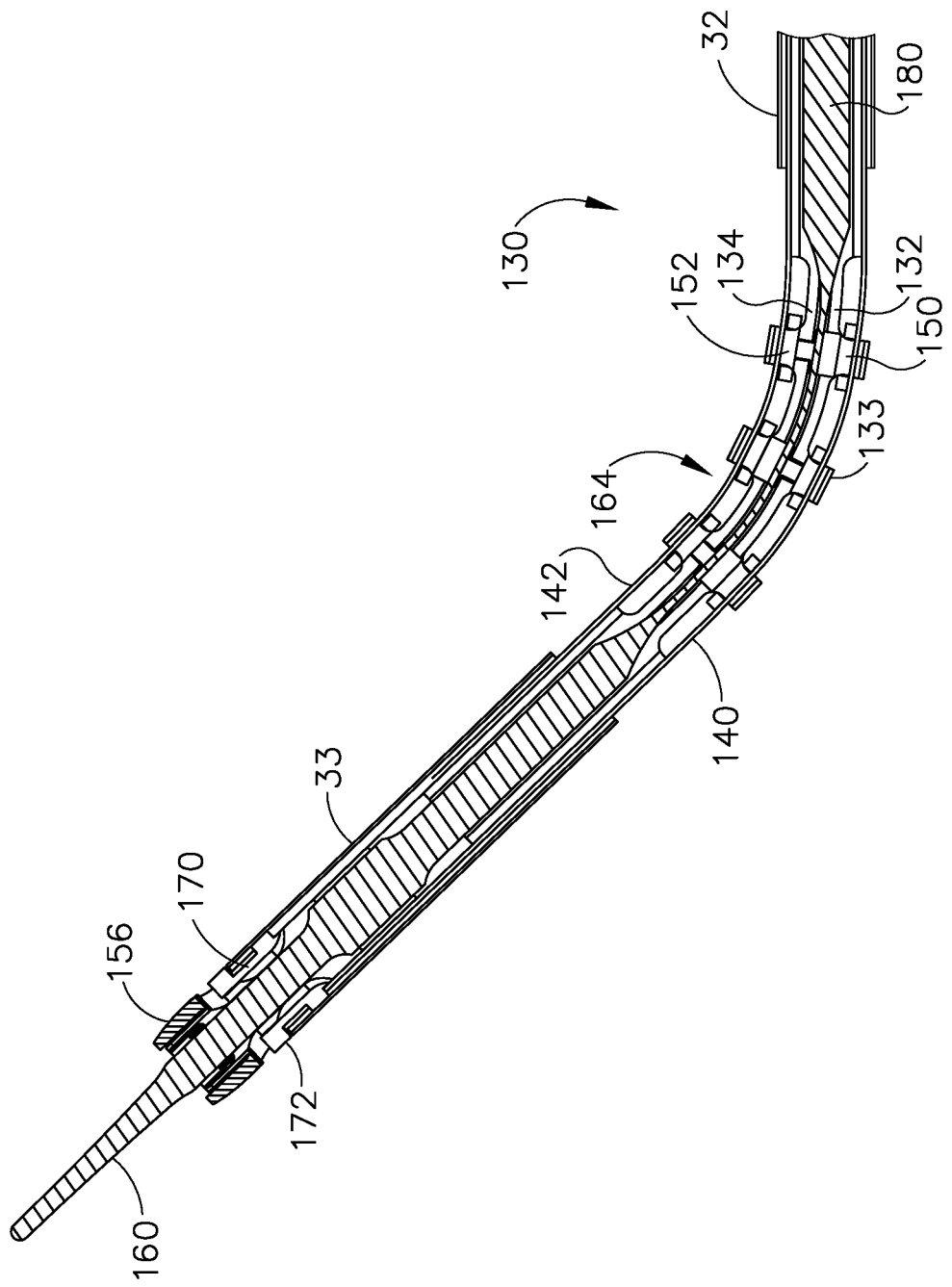
FIG. 6B depicts a cross-sectional top view of the shaft assembly and end effector of FIG. 2 in a first articulated configuration.
Figure 6C:
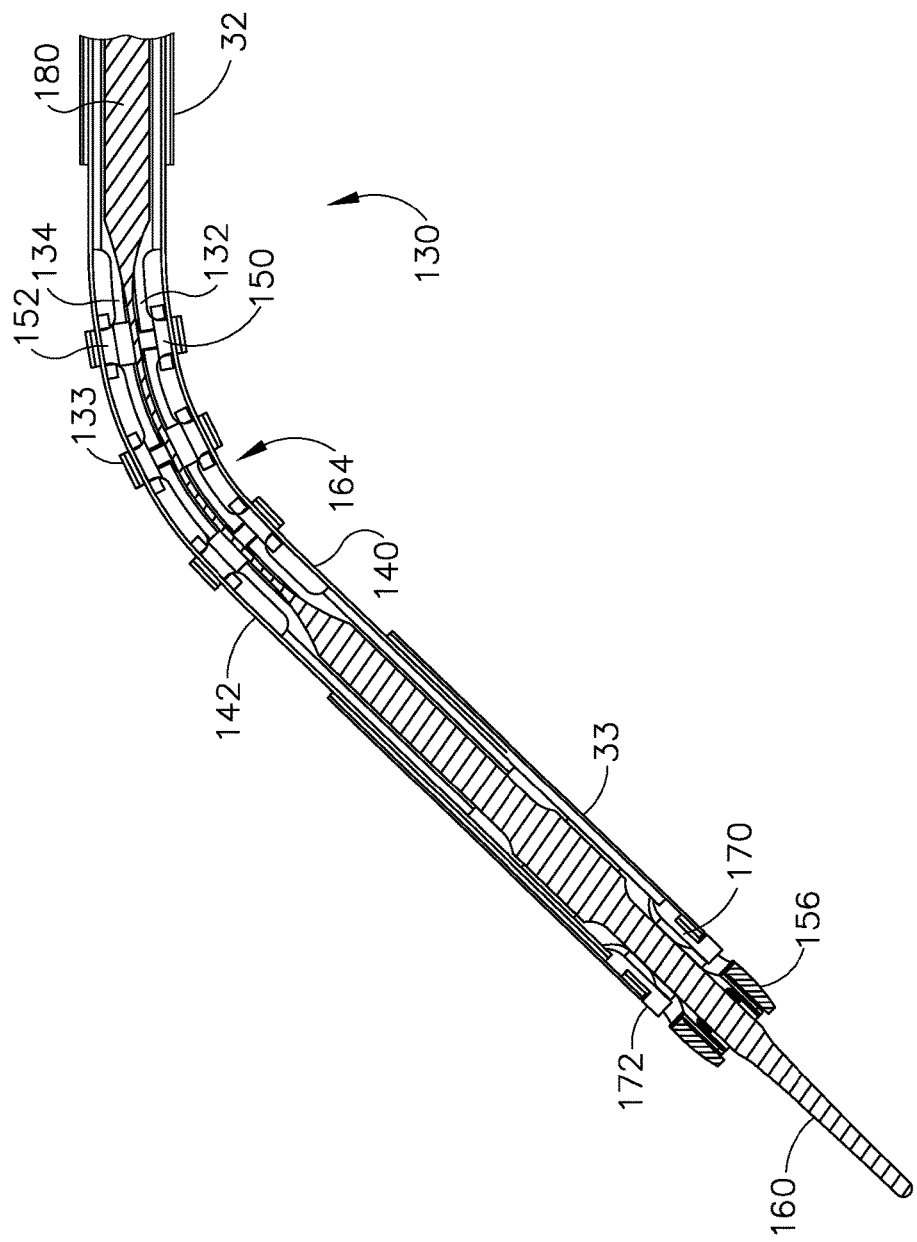
FIG. 6C depicts a cross-sectional top view of the shaft assembly and end effector of FIG. 2 in a second articulated configuration.

The distal ends of articulation bands (140, 142) are unitarily secured to upper distal shaft element (172). When articulation bands (140, 142) translate longitudinally in an opposing fashion, this will cause articulation section (130) to bend, thereby laterally deflecting end effector (40) away from the longitudinal axis of shaft assembly (30) from a straight configuration as shown in FIG. 6A to a first articulated configuration as shown in FIG. 6B; or a second articulated configuration as shown in FIG. 6C. In particular, end effector (40) will be articulated toward the articulation band (140, 142) that is being pulled proximally. During such articulation, the other articulation band (140, 142) may be pulled distally by upper distal shaft element (172). Alternatively, the other articulation band (140, 142) may be driven distally by an articulation control. Ribbed body portions (132, 134) and narrowed section (164) are all sufficiently flexible to accommodate the above-described articulation of end effector (40). Furthermore, flexible portion (166) is configured to effectively communicate ultrasonic vibrations to blade (160) even when articulation section (130) is in an articulated state as shown in FIGS. 6B-6C.

As best seen in FIG. 3, each flange (136, 138) of waveguide (180) includes a respective pair of opposing flats (192, 196). Flats (192, 196) are oriented along vertical planes that are parallel to a vertical plane extending through narrowed section (164) of flexible portion (166). Flats (192, 196) are configured to provide clearance for articulation bands (140, 142). In particular, flats (196) of proximal flange (138) accommodate articulation bands (140, 142) between proximal flange (138) and the inner diameter of proximal outer sheath (32); while flats (192) of distal flange (136) accommodate articulation bands (140, 142) between distal flange (136) and the inner diameter of distal outer sheath (33). Of course, flats (192, 196) could be substituted with a variety of features, including but not limited to slots, channels, etc., with any suitable kind of profile (e.g., square, flat, round, etc.). In the present example, flats (192, 196) are formed in a milling process, though it should be understood that any other suitable process(es) may be used. Various suitable alternative configurations and methods of forming flats (192, 196) will be apparent to those of ordinary skill in the art in view of the teachings herein. It should also be understood that waveguide (180) may include flats formed in accordance with at least some of the teachings of U.S. Pub. No. 2013/0289592, entitled "Ultrasonic Device for Cutting and Coagulating," published Oct. 31, 2013, the disclosure of which is incorporated by reference herein.

In the present example, outer rings (133) are located at longitudinal positions corresponding to ribs (150, 152), such that three rings (133) are provided for three ribs (150, 152). Articulation band (140) is laterally interposed within channel (135) between rings (133) and ribbed body portion (132); while articulation band (142) is laterally interposed within channel (137) between rings (133) and ribbed body portion (134). Rings (133) are configured to keep articulation bands (140, 142) in a parallel relationship, particularly when articulation section (130) is in a bent configuration (e.g., similar to the configuration shown in FIGS. 6B-6C). In other words, when articulation band (140) is on the inner diameter of a curved configuration presented by a bent articulation section (130), rings (133) may retain articulation band (140) such that articulation band (140) follows a curved path that complements the curved path followed by articulation band (142). It should be understood that channels (135, 137) are sized to accommodate respective articulation bands (140, 142) in such a way that articulation bands (140, 142) may still freely slide through articulation section (130), even with rings (133) being secured to ribbed body portions (150, 152). It should also be understood that rings (133) may be secured to ribbed body portions (132, 134) in various ways, including but not limited to interference fitting, adhesives, welding, etc.

When articulation bands (140, 142) are translated longitudinally in an opposing fashion, a moment is created and applied to a distal end of distal outer sheath (33) via upper distal shaft element (172). This causes articulation section (130) and narrowed section (164) of flexible portion (166) of waveguide (180) to articulate, without transferring axial forces in articulation bands (140, 142) to waveguide (180). It should be understood that one articulation band (140, 142) may be actively driven distally while the other articulation band (140, 142) is passively permitted to retract proximally. As another merely illustrative example, one articulation band (140, 142) may be actively driven proximally while the other articulation band (140, 142) is passively permitted to advance distally. As yet another merely illustrative example, one articulation band (140, 142) may be actively driven distally while the other articulation band (140, 142) is actively driven proximally. Various suitable ways in which articulation bands (140, 142) may be driven will be apparent to those of ordinary skill in the art in view of the teachings herein.

Figure 7:
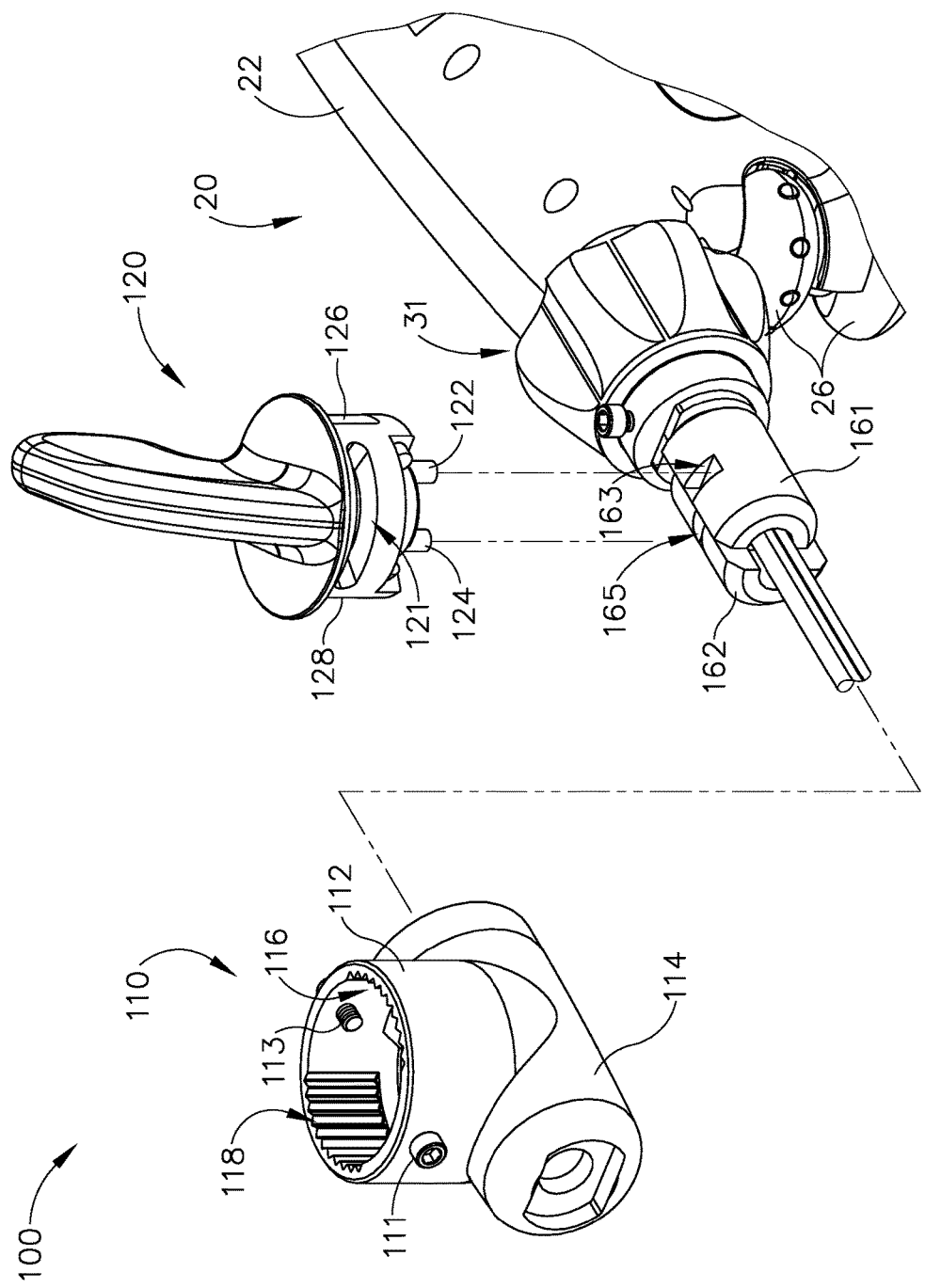
FIG. 7 depicts a partially exploded perspective view of an articulation control assembly of the surgical instrument of FIG. 1.
Figure 8:
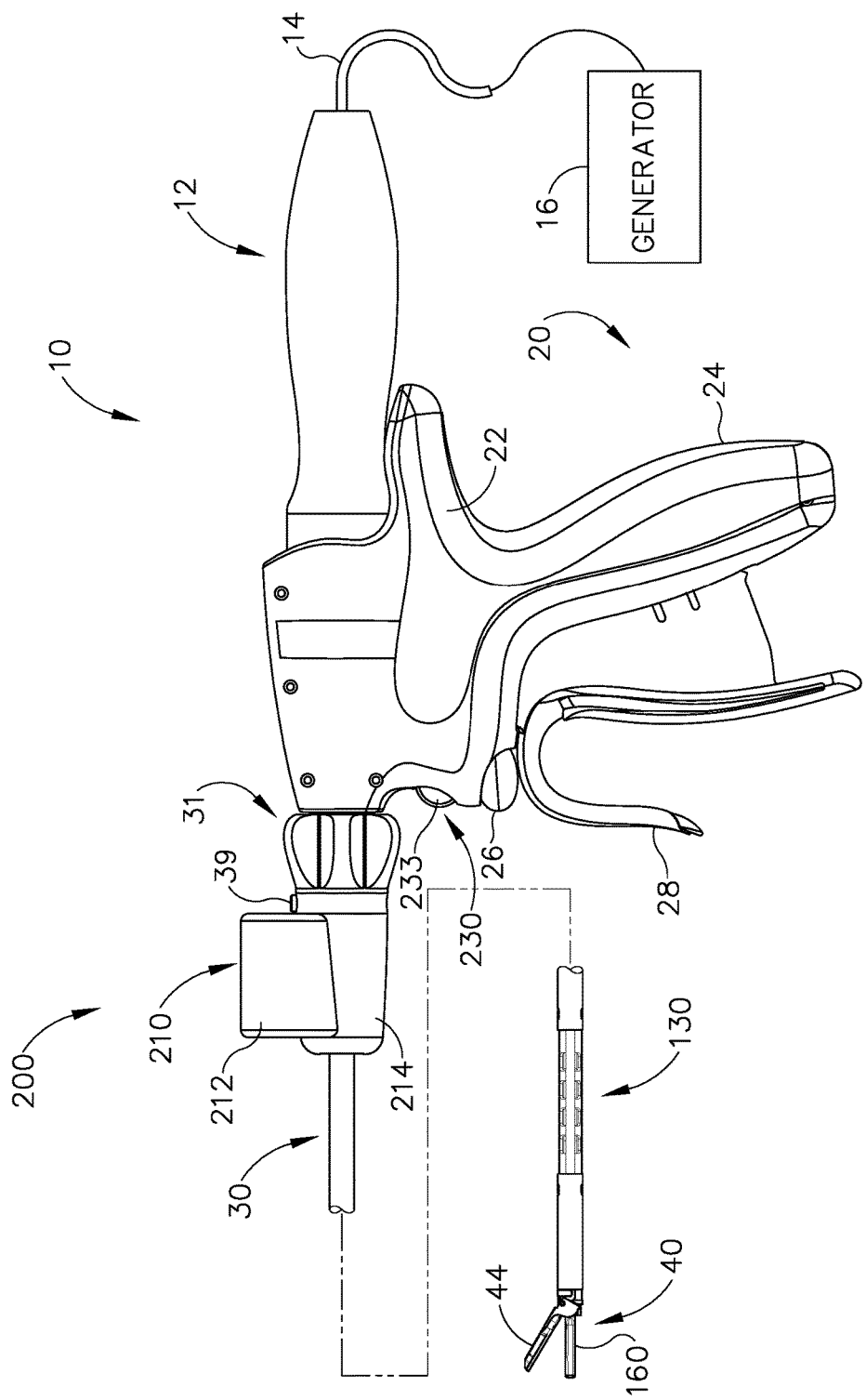
FIG. 8 depicts a side elevational view of the surgical instrument of FIG. 1 with an alternative articulation control assembly.

As best seen in FIG. 7, an articulation control assembly (100) is secured to a proximal portion of outer sheath (32). Articulation control assembly (100) comprises a housing (110) and a rotatable knob (120). Housing (110) comprises a pair of perpendicularly intersecting cylindrical portions (112, 114). Knob (120) is rotatably disposed within a first hollow cylindrical portion (112) of housing (110) such that knob (120) is operable to rotate within cylindrical portion (112) of housing (110). Shaft assembly (30) is slidably and rotatably disposed within a second cylindrical portion (114). Shaft assembly (30) comprises a pair of translatable members (161, 162), both of which extend slidably and longitudinally through the proximal portion of outer sheath (32). Translatable members (161, 162) are longitudinally translatable within second cylindrical portion (114) between a distal position and a proximal position. Translatable members (161, 162) are mechanically coupled with respective articulation bands (140, 142) such that longitudinal translation of translatable member (161) causes longitudinal translation of articulation band (140), and such that longitudinal translation of translatable member (162) causes longitudinal translation of articulation band (142).

Knob (120) comprises a pair of pins (122, 124) extending downwardly from a bottom surface of knob (120). Pins (122, 124) extend into second cylindrical portion (114) of housing (110) and are rotatably and slidably disposed within a respective pair of channels (163, 165) formed in top surfaces of translatable members (161, 162). Channels (163, 165) are positioned on opposite sides of an axis of rotation of knob (120), such that rotation of knob (120) about that axis causes opposing longitudinal translation of translatable members (161, 162). For instance, rotation of knob (120) in a first direction causes distal longitudinal translation of translatable member (161) and articulation band (140), and proximal longitudinal translation of translatable member (162) and articulation band (142); and rotation of knob (120) in a second direction causes proximal longitudinal translation of translatable member (161) and articulation band (140), and distal longitudinal translation of translatable member (162) and articulation band (142). Thus, it should be understood that rotation of rotation knob (120) causes articulation of articulation section (130).

Housing (110) of articulation control assembly (100) comprises a pair of set screws (111, 113) extending inwardly from an interior surface of first cylindrical portion (112). With knob (120) rotatably disposed within first cylindrical portion (112) of housing (110), set screws (111, 113) are slidably disposed within a pair of arcuate channels (121, 123) formed in knob (120). Thus, it should be understood that rotation of knob (120) will be limited by movement of set screws (111, 113) within channels (121). Set screws (111, 113) also retain knob (120) in housing (110), preventing knob (120) from traveling vertically within first cylindrical portion (112) of housing (110).

An interior surface of first cylindrical portion (112) of housing (110) comprises a first angular array of teeth (116) and a second angular array of teeth (118) formed in an interior surface of first cylindrical portion (112). Rotation knob (120) comprises a pair of outwardly extending engagement members (126, 128) that are configured to engage teeth (116, 118) of first cylindrical portion (112) in a detent relationship to thereby selectively lock knob (120) in a particular rotational position. The engagement of engagement members (126, 128) with teeth (116, 118) may be overcome by a user applying sufficient rotational force to knob (120); but absent such force, the engagement will suffice to maintain the straight or articulated configuration of articulation section (130). It should therefore be understood that the ability to selectively lock knob (120) in a particular rotational position lock will enable an operator to selectively lock articulation section (130) in a particular deflected position relative to the longitudinal axis defined by outer sheath (32).

In addition to or in lieu of the foregoing, articulation section (130) and/or articulation control assembly (100) may be constructed and/or operable in accordance with at least some of the teachings of U.S. patent application Ser. No. 14/688,458, entitled "Ultrasonic Surgical Instrument with Rigidizing Articulation Drive Members," filed on Apr. 16, 2015. Alternatively, articulation section (130) and/or articulation control assembly (100) may be constructed and/or operable in any other suitable fashion.

II. Exemplary Alternative Motorized Articulation Control

In some instances, it may be desirable to drive the articulation of a shaft assembly of an ultrasonic instrument through motorized controls. Providing motorized articulation control may improve the ergonomics of an ultrasonic instrument with articulation features. For instance, motorized articulation may reduce the user-applied force required to selectively position end effector (40) at various lateral deflection angles relative to the longitudinal axis defined by outer sheath (32). Reducing the amount of force required for a user to articulate end effector (40) may provide additional overall control and stability of instrument (10) during use. Additionally, a button or multiple buttons controlling motorized articulation may be located adjacent to trigger (28) such that a user may pivot trigger (28) toward and away from pistol grip (24) and activate motorized articulation with the same hand.

FIGS. 8-12C show an alternative articulation control assembly (200) that may be readily incorporated into instrument (10) described above. As best seen in FIGS. 9 and 11A-11C, articulation control assembly (200) includes a housing (210), a drive assembly (220), and a motor control assembly (230). Housing (210) includes a lower cylindrical portion (214) defining a pair of openings (216, 218), and an upper conical portion (212). Upper conical portion (212) and lower cylindrical portion (214) together define a cavity (211) that contains a portion of shaft assembly (30) and at least a portion of drive assembly (220).

Figure 11A:
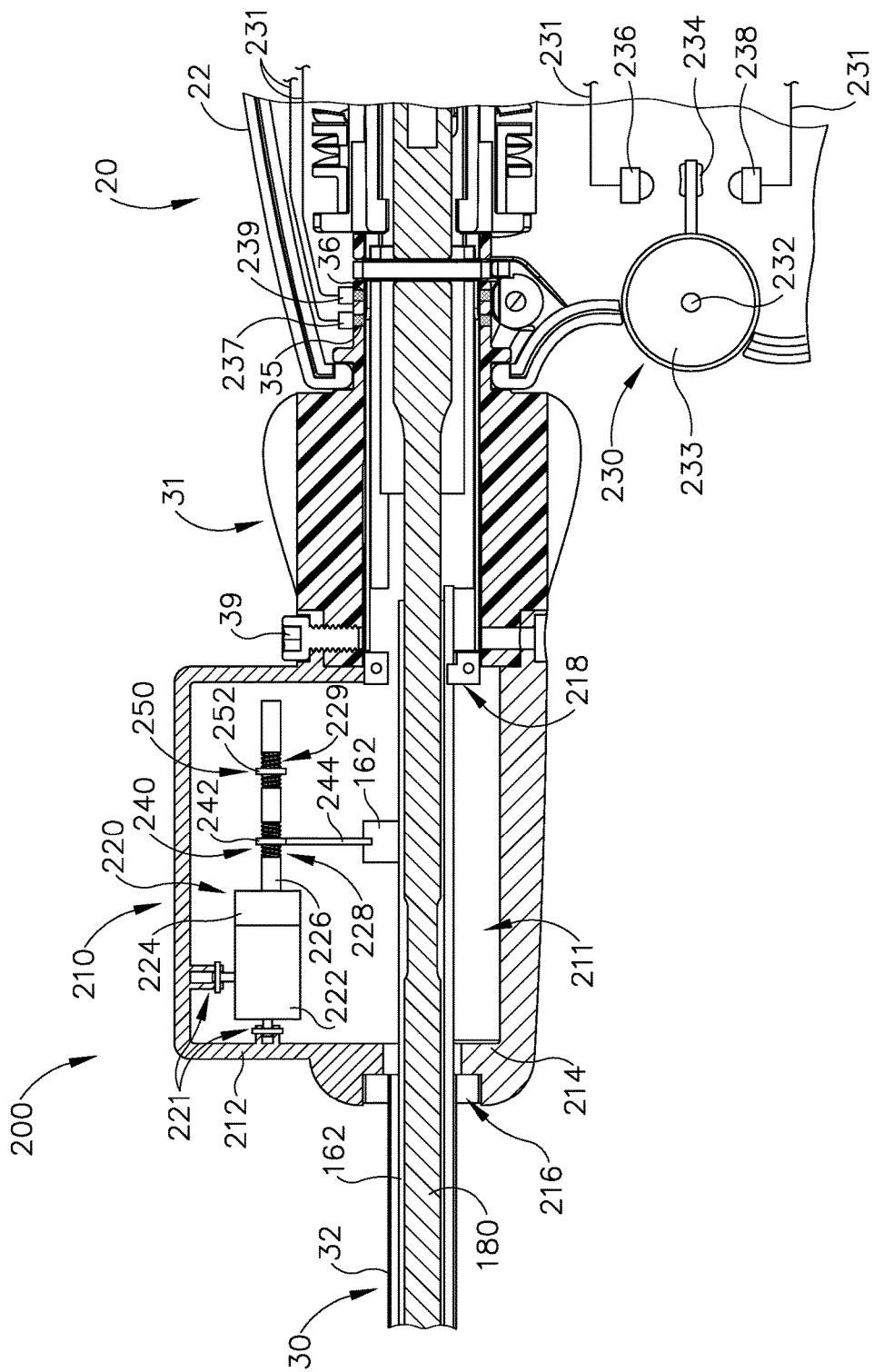
FIG. 11A depicts a cross-sectional side view, taken along line 11A-11A of FIG. 10, of the articulation control assembly of FIG. 8, where the articulation control assembly is in a first configuration associated with the shaft assembly and end effector of FIG. 2 in the straight configuration shown in FIG. 6A.
Figure 11B:
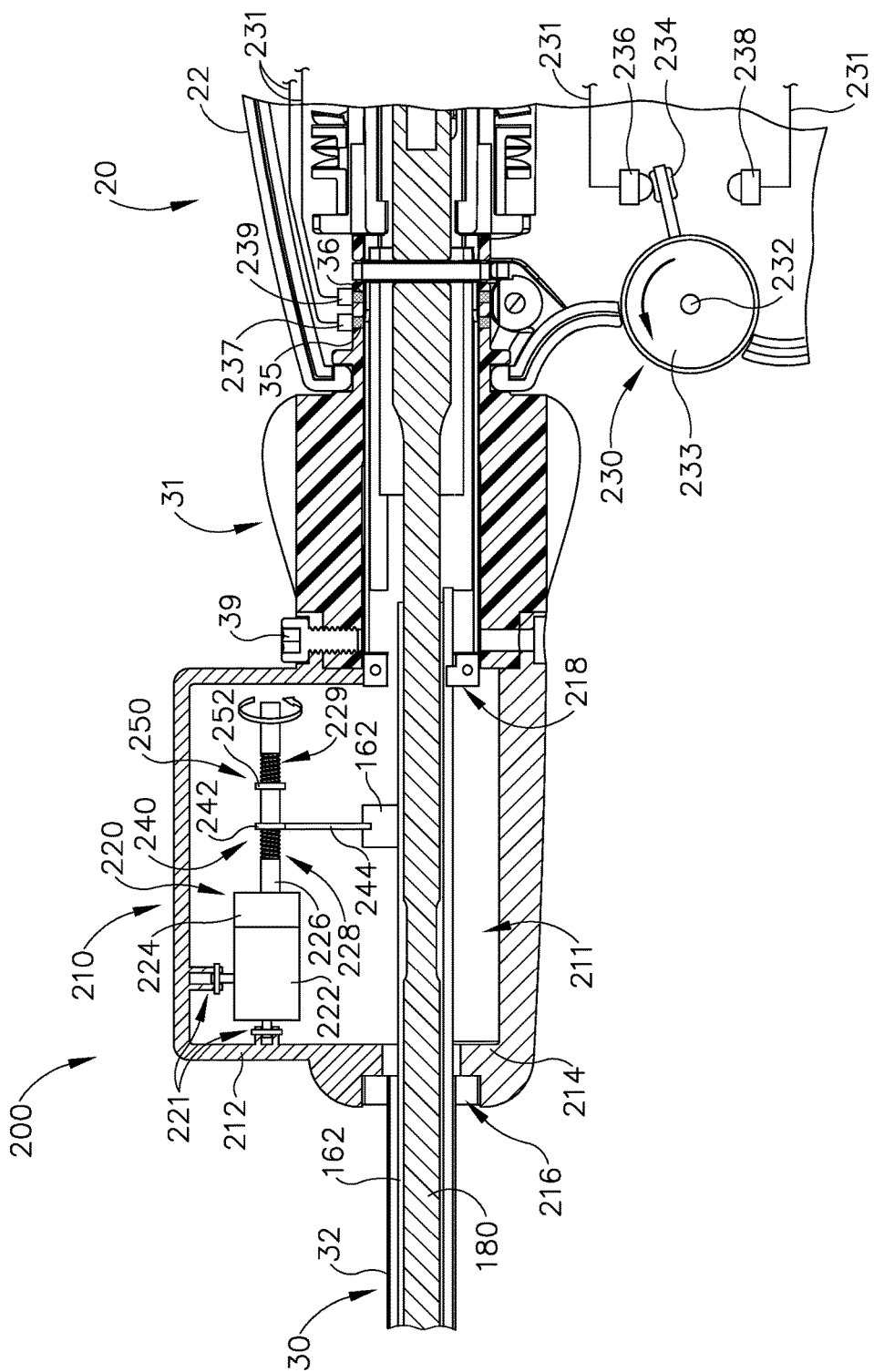
FIG. 11B depicts a cross-sectional side view, taken along line 11A-1A of FIG. 10, of the articulation control assembly of FIG. 8, where the articulation control assembly is in a second configuration associated with the shaft assembly and end effector of FIG. 2 in the first articulated configuration shown in FIG. 6B.
Figure 11C:
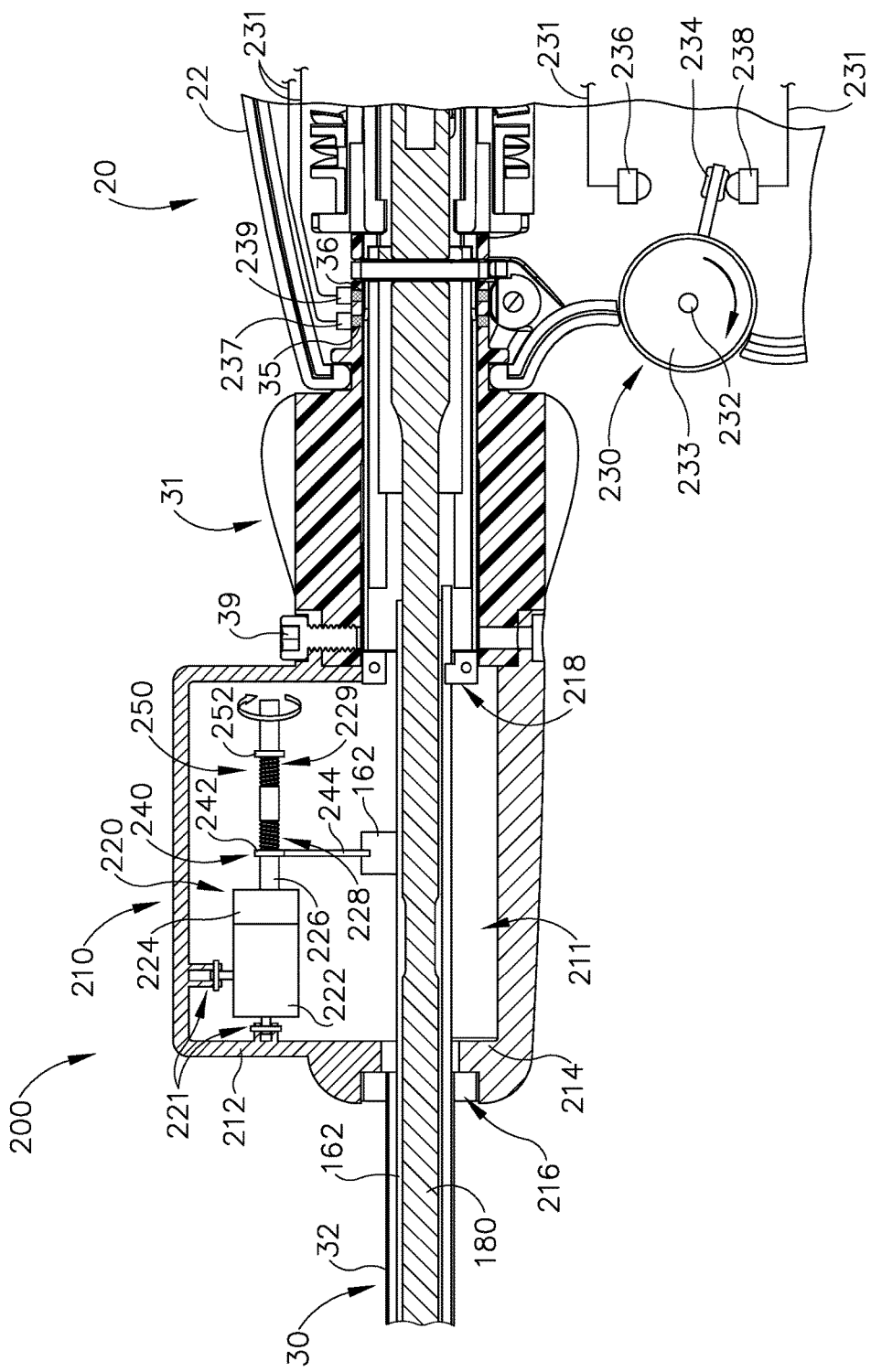
FIG. 11C depicts a cross-sectional side view, taken along line 11A-11A of FIG. 10, of the articulation control assembly of FIG. 8, where the articulation control assembly is in a third configuration associated with the shaft assembly and end effector of FIG. 2 in the second articulation configuration shown in FIG. 6C.

Shaft assembly (30) extends through openings (216, 218) defined by lower cylindrical portion (214). Therefore, shaft assembly (30) is partially housed within the portion of cavity (211) defined by lower cylindrical portion (214). Additionally, at least a portion of shaft assembly (30) is slidably disposed within lower cylindrical portion (214). As best seen in FIGS. 11A-11C, housing (210) is fixed to knob (31) by a coupling screw (39), though of course any other suitable components or techniques may be used to secure housing (210) to knob (31). As mentioned above, knob (31) is rotatable relative to body (22), such that shaft assembly (30) is rotatable about the longitudinal axis defined by outer sheath (32), relative to handle assembly (20). Therefore, housing (210) is also rotatable about the longitudinal axis defined by outer sheath (32). Of course, rotatable features may simply be omitted if desired, such that housing (210) may be fixed to or within body (22) if knob (31) is omitted.

Drive assembly (220) is housed within upper conical portion (212) of housing (210). Upper conical portion (212) may be removably coupled to lower cylindrical portion (214) in order to install drive assembly (220) within housing (210). For instance, upper conical portion (212) may have snap fit features that are configured to mate with complementary slots of lower cylindrical portion (214). Upper conical portion (212) may be made out of a resilient material, enabling a user to deform upper conical portion (212) such that snap fit features align with complementary slots, thereby enabling a user to remove upper conical portion (212) from lower cylindrical portion (214). Other suitable coupling features will be apparent to one having ordinary skill in the art in view of the teachings herein. Upper conical portion (212) may be permanently fixed to lower cylindrical portion (210) after drive assembly (220) is installed within housing (210). Alternatively, upper conical portion (212) may have its own opening (not shown) to receive drive assembly (220) such that drive assembly (220) may be installed within housing (210) while upper conical portion (212) and lower cylindrical portion (214) are already fixed together. It should be understood that while conical and cylindrical shapes are used in the present example, any other suitable geometric shapes may be used for upper conical portion (212) and lower cylindrical portion (214) as would be apparent to one having ordinary skill in the art in view of the teachings herein.

Drive assembly (220) includes a motor (222), a gear box (224), a drive shaft (226), a first drive member (240), and a second drive member (250). As will be described in greater detail below, drive assembly (220) is configured to selectively translate articulation bands (140, 142) longitudinally in an opposing fashion to laterally deflect end effector (40) away from the longitudinal axis of shaft assembly (30).

Motor (222) is operable to rotate drive shaft (226) about the longitudinal axis defined by drive shaft (226) in a clockwise or counterclockwise direction. Motor (222) is configured to generate a predetermined output torque and transfer that torque to gearbox (224). Gearbox (224) converts the torque generated by motor (222) to a desired amount of torque and transfers the desired torque to drive shaft (226) in order to rotate drive shaft (226). Various suitable components and configurations that may be incorporated into gearbox (224) will be apparent to those of ordinary skill in the art in view of the teachings herein. If the predetermined output torque generated by motor is equal to the desired torque to be transferred to drive shaft (226), then drive shaft (226) may be directly connected to motor (222), such that gearbox (224) may be omitted in some versions. Any other suitable manner of rotating drive shaft (226) may be used as would be apparent to one having ordinary skill in the art in view of the teachings herein.

As best seen in FIGS. 11A-11C, motor (222) may be fixedly coupled to housing (210) via mounts (221). While two mounts (221) are shown in the present example, any suitable number of mount(s) (221) may be utilized as would be apparent to one having ordinary skill in the art in view of the teachings herein. Because motor (222) is fixedly coupled to housing (210), rotation of housing (210) about the longitudinal axis defined by outer sheath (32) also rotates drive assembly (220) about the longitudinal axis defined by outer sheath (32). While mounts (221) are used in the current example, any other suitable method of fixing motor (222) to housing (210) may be utilized as would be apparent to one having ordinary skill in the art in view of the teachings herein.

Drive shaft (226) includes a first threaded portion (228) and a second threaded portion (229). First threaded portion (228) and second threaded portion (229) are threaded in opposite directions relative to each other, such that threaded portions (228, 229) have opposing pitch orientations. For instance, in versions where first threaded portion (228) is threaded in a right-handed configuration, second threaded portion (229) would be threaded in a left-handed configuration. Alternatively, in versions where first threaded portion (228) is threaded in a left-handed configuration, second threaded portion (229) would be threaded in a right-handed configuration.

Figure 9:
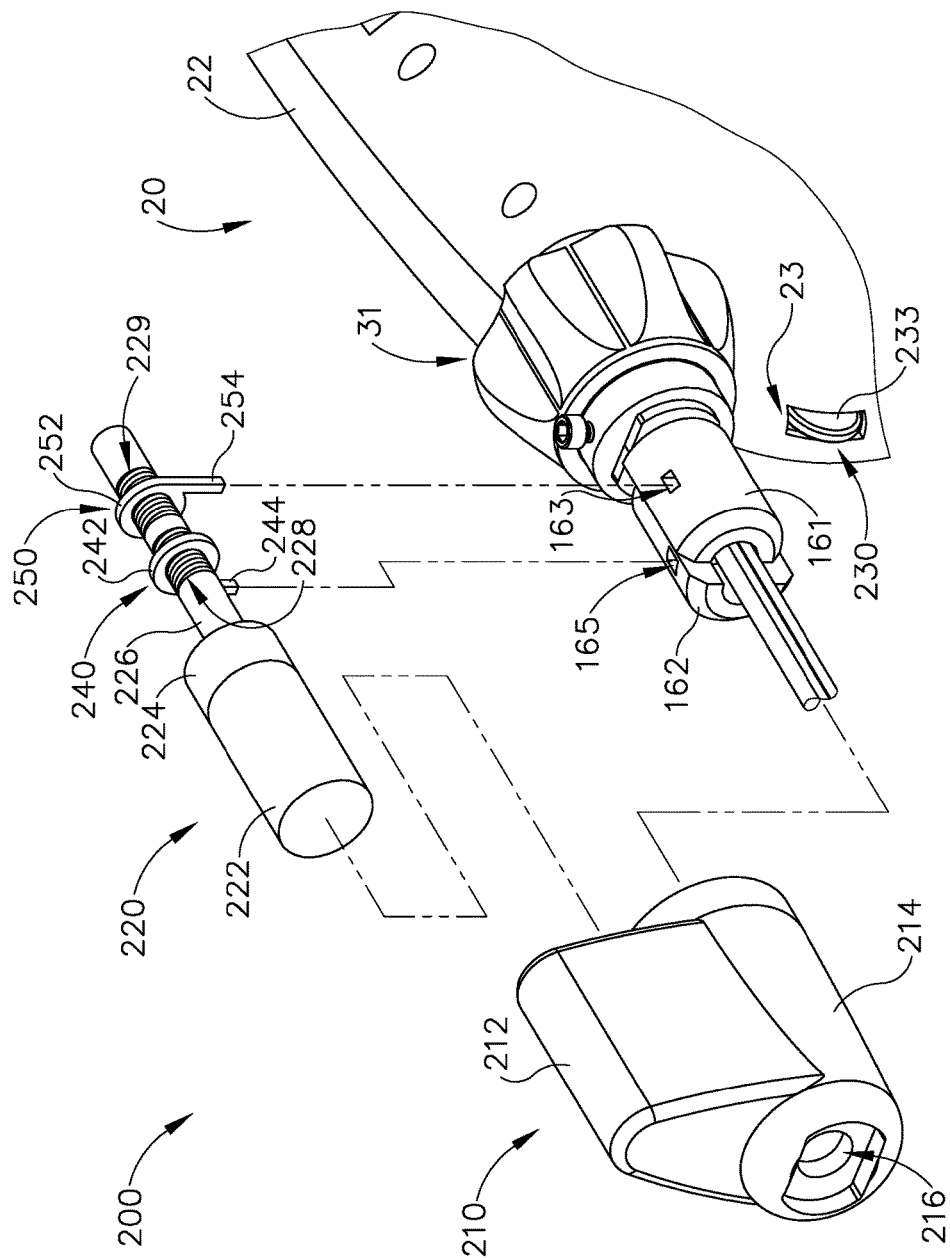
FIG. 9 depicts a partially exploded perspective view of the articulation control assembly of FIG. 8.
Figure 10:
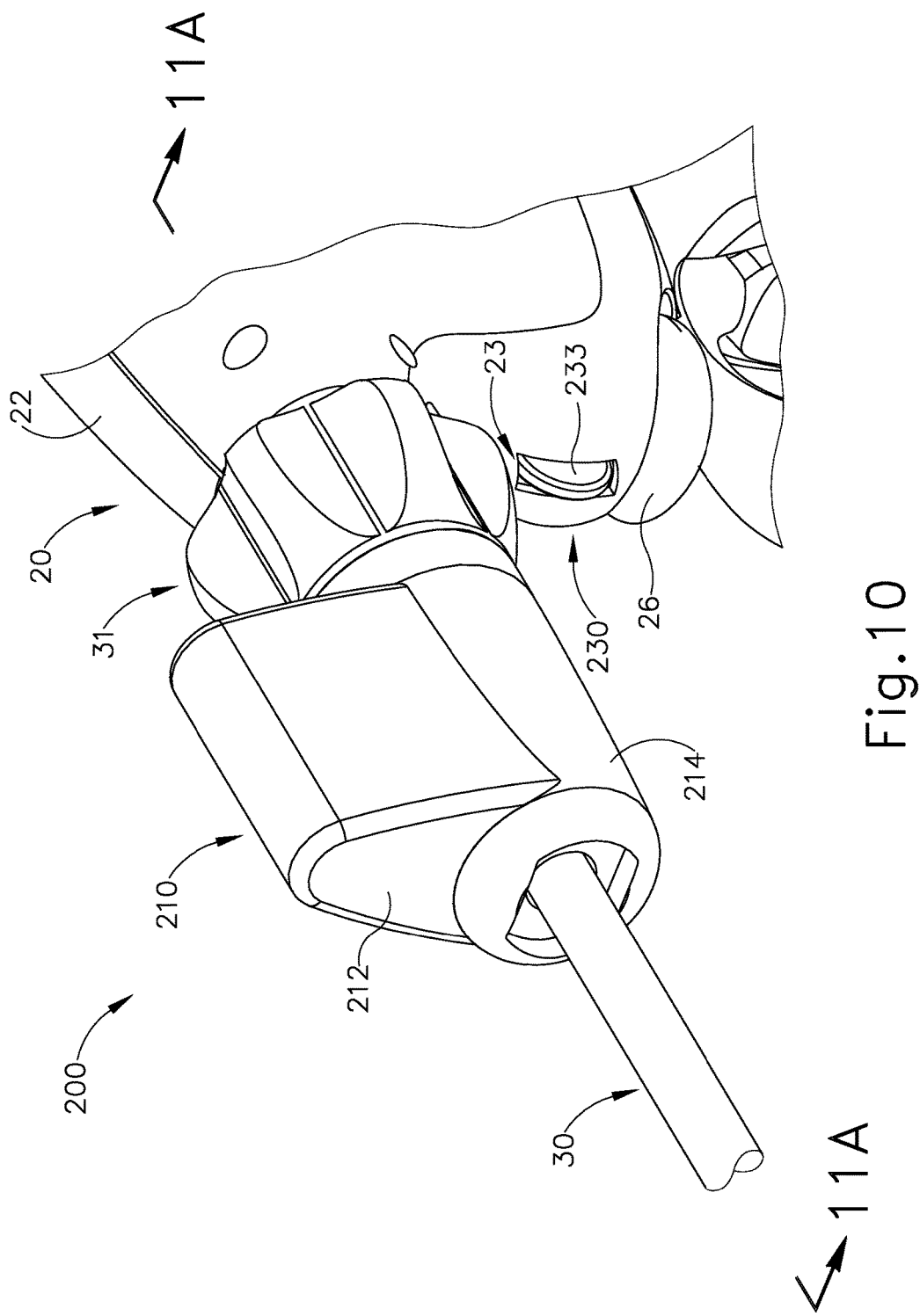
FIG. 10 depicts a partial perspective view of the surgical instrument of FIG. 1 with the articulation control assembly of FIG. 8.

First drive member (240) includes a threaded ring (242) and a pin (244). Similarly, second drive member (250)

includes a threaded ring (252) and a pin (254). Threaded ring (242) includes threading that is complementary to first threaded portion (228) while threaded ring (252) includes threading that is complementary to second threaded portion (229). Pins (244, 253) are fixed to their respective threaded ring (242, 252). Additionally, as shown in FIG. 9, pins (244, 254) extend from threaded rings (242, 252) into channels (165, 163) defined by translatable members (162, 161), respectively.

Channel (165) mechanically grounds first drive member (240) to prevent first drive member (240) from rotating about drive shaft (226). Additionally, channel (163) mechanically grounds second drive member (250) to prevent second drive member (250) from rotating about drive shaft (226). Therefore, as motor (222) and gearbox (224) rotate drive shaft (226), drive members (240, 250) travel simultaneously along their respective threaded portions (228, 229) due to the engagement between threaded portions (228, 229) and threaded rings (242, 252). In other words, rotation of drive shaft (226) moves drive members (240, 250) simultaneously along their respective threaded portions (228, 229). As mentioned above, first threaded portion (228) and second threaded portion (229) are threaded in opposite directions relative to each other. Therefore, rotation of drive shaft (226) moves drive members (240, 250) along their respective threaded portions (228, 229) in opposite longitudinal directions, such that drive member (240) translates distally while drive member (250) simultaneously translates proximally; and such that drive member (240) translates proximally while drive member (250) simultaneously translates distally.

Because pin (244) extends into channel (165) of translatable member (162), translation of first drive member (240) along first threaded portion (228) also actuates translatable member (162) in a first direction. Because pin (254) extends into channel (163) of translatable member (161), translation of second drive member (250) along second threaded portion (229) also actuates translatable member (161) in a second direction. Again, because the first threaded portion (228) and the second threaded portion (229) are threaded in opposite directions relative to each other, translatable members (161, 162) also translate in opposing longitudinal directions.

Translatable members (161, 162) extend slidably and longitudinally through outer sheath (32) and terminate within cavity (211) defined by housing (210). The proximal end of outer sheath (32) is fixed to the portion of cylindrical portion (214) defining opening (216). As mentioned above, translatable members (161, 162) are mechanically coupled with respective articulation bands (140, 142) such that longitudinal translation of translatable member (161) causes longitudinal translation of articulation band (140), and such that longitudinal translation of translatable member (162) causes longitudinal translation of articulation band (142). When articulation bands (140, 142) are translated longitudinally in an opposing fashion, a moment is created and applied to a distal end of distal outer sheath (33) via upper distal shaft element (172). This causes articulation section (130) and narrowed section (164) of flexible portion (166) of waveguide (180) to articulate, without transferring axial forces in articulation bands (140, 142) to waveguide (180).

As mentioned above, rotation of knob (31) and housing (210) about the longitudinal axis defined by outer sheath (32) also rotates drive assembly (220) about the longitudinal axis defined by outer sheath (32). It should be understood that rotation of knob (31) also unitarily rotates shaft assembly (30), including translatable members (161, 162) and their channels (163, 165). Because rotation of knob (31) causes drive shaft (226), first drive member (240), second drive member (250), and translatable members (161, 162) to unitarily rotate about the longitudinal axis defined by outer sheath (32), rotation of knob (31) does not cause relative rotation between threaded rings (242, 252) and threaded sections (228, 229). In other words, rotation of knob (31) does not cause inadvertent articulation of end effector (40).

As best seen in FIGS. 11A-11C, motor control assembly (230) includes a wheel (233) rotatably fixed to body (22) via pivot (232), a switch arm (234), a first switch (236), a second switch (238), a pair of brush connectors (237, 239), a pair of slip ring connectors (35, 36), and a plurality of wires (231). Wheel (233) extends out of slot (23) defined by body (22) such that a user may manipulate wheel (233) with a finger of the same hand that grasps instrument (10) via pistol grip (24). However, wheel (233) may alternatively be located at any other suitable location as would be apparent to one having ordinary skill in the art in view of the teachings herein.

Switch arm (234) is fixed to wheel (233) and extends radially outwardly from a portion of wheel (233) located inside body (22) toward first switch (236) and second switch (238). As will be described in greater detail below, activation of first switch (236) will activate motor (222) to rotate shaft assembly (226) in a first rotational direction; while activation of second switch (238) will activate motor (222) to rotate shaft assembly (226) in a second, opposite, rotational direction. Thus, rotation of wheel (230) in a first direction will activate first switch (236) to drive articulation of end effector (40) in a one direction; while rotation of wheel (230) in a second direction will activate second switch (238) to drive articulation of end effector (40) in a second direction.

First switch (236) and second switch (238) are fixed to body (22). Switch arm (234) is disposed between first switch (236) and second switch (238). Wheel (233) may be rotated such that switch arm (234) may contact either first switch (236) or second switch (238). In some versions, wheel (233) may be biased to the position shown in FIG. 11A so that when a user does not manipulate wheel (233), wheel (233) does not contact either first switch (236) or second switch (238). Wheel (233) may be biased with a torsion spring (not shown) or any other suitable biasing mechanism known to one in the art in view of the teachings herein. When wheel (233) is in the neutral position shown in FIG. 11A, motor (222) does not drive articulation of end effector (40) through rotation of shaft assembly (226). As a result, articulation section (130) may remain in a static state (e.g., in a straight configuration or in a bent configuration).

Brush connectors (237, 239) are fixed relative to body (22). Additionally, brush connectors (237, 239) are in electrical communication with first switch (236) and second switch (238) via wires (231). Brush connectors (237, 239) make contact, and thereby provide electrical communication, with slip ring connectors (35, 36) respectively. In the current example, slip ring connectors (35, 36) are an integral component of knob (31) and circumferentially encompass a portion of knob (31). Thus, brush connectors (237, 239) maintain contact and electrical continuity with their respective slip ring connectors (35, 36) as knob (31) is rotated. Alternatively, slip ring connectors (35, 36) may be an integral component of shaft assembly (30) or any other suitable location that would be apparent to one having ordinary skill in the art in view of the teachings herein.

Slip ring connectors (35, 36) are in electrical communication with motor (222) via electrical traces (not shown) embedded within knob (31) and housing (210) and/or via one or more wires (not shown) extending through knob (31)

and housing (210). First switch (236) and second switch (238) are thus in electrical communication with motor (222) via wires (231), brush connectors (237, 239), slip ring connectors (35, 36), and electrical traces (not shown). Alternatively, slip ring connectors (35, 36) may be in electrical communication with motor (222) utilizing any other suitable components as would be apparent to one having ordinary skill in the art in view of the teachings herein.

While brush connectors (237, 239) provide electrical communication between wires (231) and slip ring connectors (35, 36) in the current example, it should be understood that any other suitable type of electrical connection may be used between wires and slip ring connectors (35, 36) as would be apparent to one having ordinary skill in the art in view of the teachings herein. For example, a spring biased ball bearing may be utilized to provide electrical communication between wires (231) and slip ring connectors (35, 36). As another merely illustrative example, brush connectors (237, 239) may be replaced with leaf springs or other features that are configured to provide both sliding contact and electrical continuity. As yet another merely illustrative example, an inductive coupling may be used. Still other suitable features and configurations that may be used to substitute or supplement brush connectors (237, 239) and/or slip ring connectors (35, 36) will be apparent to those of ordinary skill in the art in view of the teachings herein.

While the current example shows wheel (233) being capable of activating either first switch (236) or second switch (238), it should be understood that wheel (233) is merely optional. For instance, first switch (236) and second switch (238) may be placed on the outside of body (22). In such versions, a user may compress either first switch (236) or second switch (238) depending on the desired direction of articulation. While the current example shows wheel (233) rotating such that the circumferential surface of wheel (233) along a vertical plane, wheel (233) may rotate about an axis such that the circumferential surface of wheel (233) travels along a vertical plane. In other words, while wheel (233) rotates about a horizontal axis in the present example, in some other versions wheel (233) may instead rotate about a vertical axis. Other suitable configurations and arrangements will be apparent to those of ordinary skill in the art in view of the teachings herein.

Figure 12A:
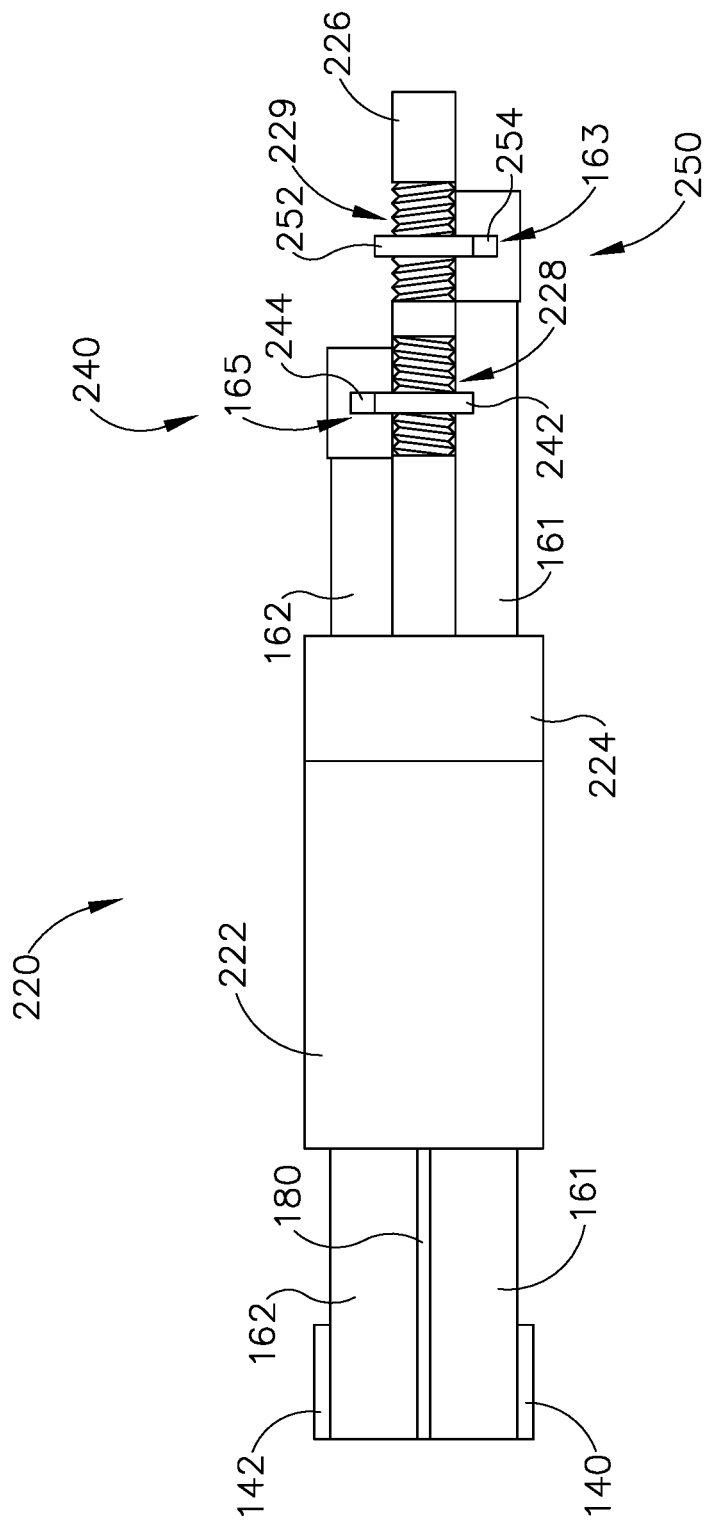
FIG. 12A depicts a top plan view of the articulation control assembly of FIG. 8 without the housing, where the articulation control assembly is in a first configuration associated with the shaft assembly and end effector of FIG. 2 in the straight configuration shown in FIG. 6A.
Figure 12B:
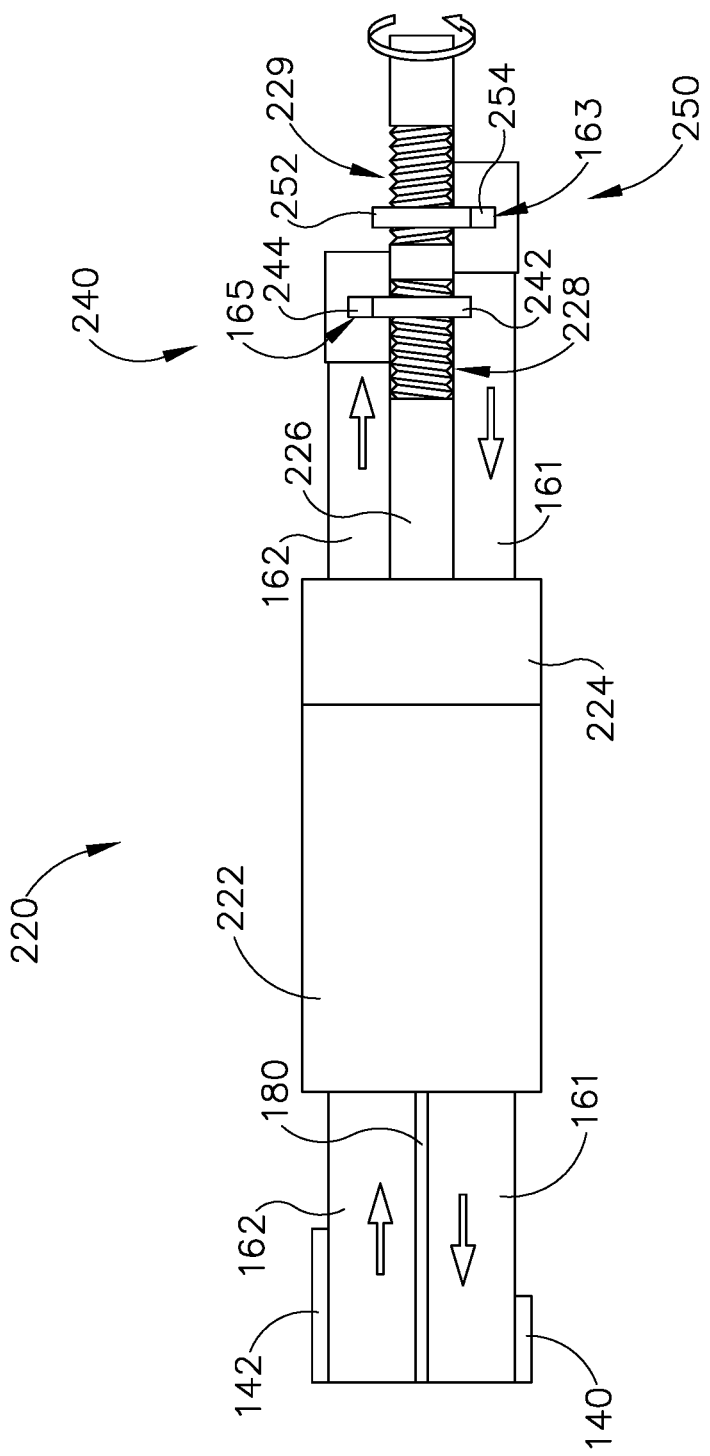
FIG. 12B depicts a top plan view of the articulation control assembly of FIG. 8 without the housing, where the articulation control assembly is in a second configuration associated with the shaft assembly and end effector of FIG. 2 in the first articulated configuration shown in FIG. 6B.
Figure 12C:
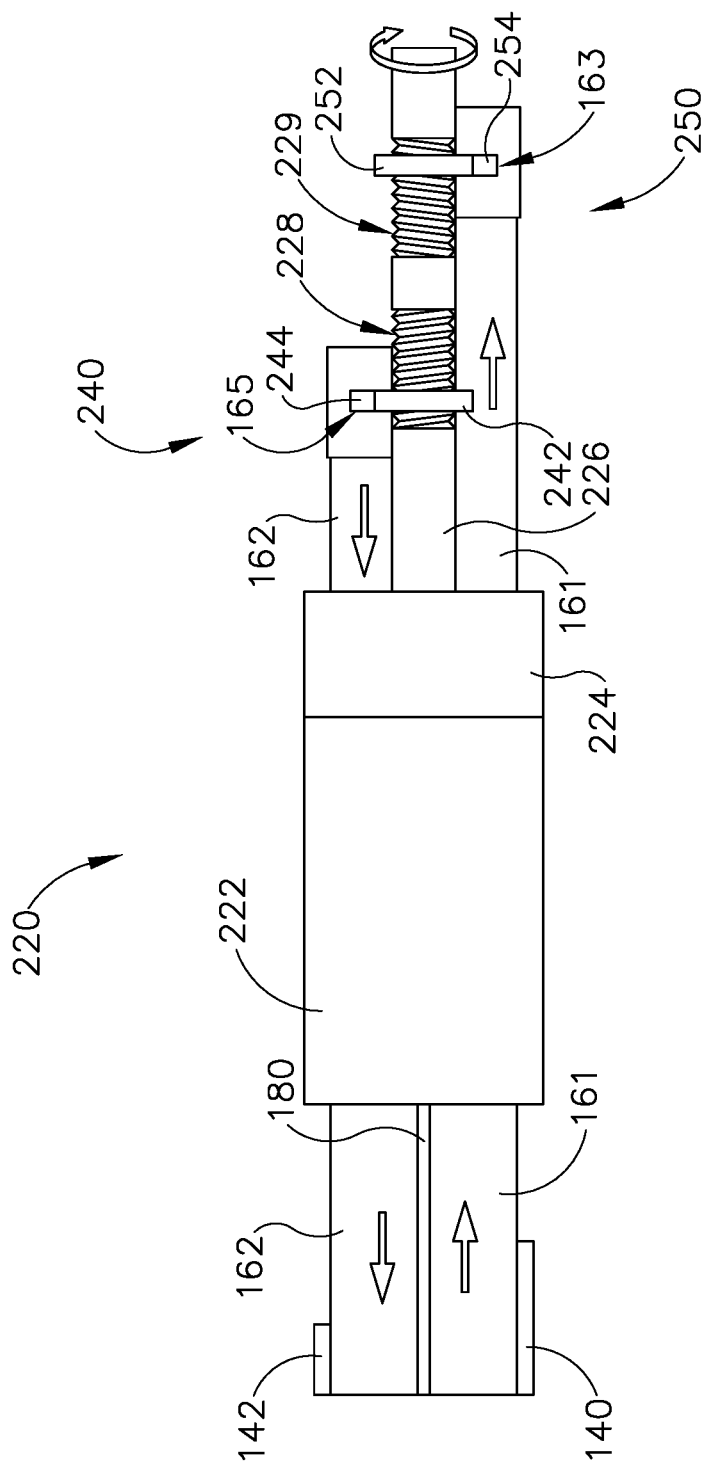
FIG. 12C depicts a top plan view of the articulation control assembly of FIG. 8 without the housing, where the articulation control assembly is in a third configuration associated with the shaft assembly and end effector of FIG. 2 in the second articulation configuration shown in FIG. 6C.

FIGS. 11A-11C show an exemplary use of motorized articulation control assembly (200). Additionally, FIGS. 12A-12C show the same exemplary use of motorized articulation control assembly without housing (210) or outer shaft (32) for clarity. FIGS. 11A and 12A show motorized articulation control assembly (200) when articulation section (130) is in an unarticulated state. The position of end effector (40) corresponding to the state shown in FIGS. 11A and 12A is shown in FIG. 6A. In the unarticulated state, translatable members (161, 162) are positioned such that the distal ends of articulation bands (140, 142) do not impart a moment to a distal end of outer sheath (33) via upper distal shaft element (172). As can be seen in FIGS. 11A and 12A, threaded rings (242, 253) are located in the middle of their respective threaded regions (228, 229), although this is not entirely necessary.

As shown in FIG. 11B, a user may rotate wheel (233) such that switch arm (234) contacts first switch (236). First switch (236) may activate motor (222) to rotate drive shaft (226) in a first rotational direction. First switch (236) may send a signal through wires (231) to brush connectors (237, 239). Brush connectors (237, 239) communicate the signal through slip ring connectors (35, 36) and electrical tracing to motor (222) in order to activate motor (222) in a first rotational direction. As described above and shown in FIGS. 11B and 12B, motor (222) drives shaft assembly (226) in a first rotational direction. This in turn causes drive members (240, 250) to translate in opposite longitudinal directions. In particular, first drive member (240) translates in the proximal direction while second drive member (250) translates in the distal direction. Therefore, translatable member (162) and articulation band (142) translate in the proximal direction while translatable member (161) and articulation band (140) translate in the distal direction. The position of end effector (40) corresponding to the state shown in FIGS. 11B and 12B is shown in FIG. 6B. In this first articulated state, translatable members (161, 162) are positioned such that the distal ends of articulation bands (140, 142) do impart a moment to a distal end of outer sheath (33) via upper distal shaft element (172).

Alternatively, as shown in FIG. 11C, a user may rotate wheel (233) such that switch arm (234) contacts second switch (238). Second switch (238) may activate motor (222) to rotate drive shaft (226) in a second rotational direction. Second switch (238) may send a signal through wires (231) to brush connectors (237, 239). Brush connectors (237, 239) communicate the signal through slip ring connectors (35, 36) and electrical tracing to motor (222) in order to activate motor (222) in a second rotational direction. As described above and shown in FIGS. 11C and 12C, motor (222) drives shaft assembly (226) in a second rotational direction. This in turn causes drive members (240, 250) to translate in opposite longitudinal directions. In particular, first drive member (240) translates in the distal direction while second drive member (250) translates in the proximal direction. Therefore, translatable member (162) and articulation band (142) translate in the distal direction while translatable member (161) and articulation band (140) translate in the proximal direction. The position of end effector (40) corresponding to the state shown in FIGS. 11C and 12C is shown in FIG. 6C. In this second articulated state, translatable members (161, 162) are positioned such that the distal ends of articulation bands (140, 142) do impart a moment to a distal end of outer sheath (33) via upper distal shaft element (172).

While the articulated positions shown in FIGS. 6B-6C are described above as being the first articulated state and the second articulated state, it should be understood that articulation control (200) may drive end effector to a plurality of articulated states located between the first and second articulated positions shown in FIGS. 6B-6C. It should be understood that degree and/or speed at which end effector may articulate may be determined by the pitch of first threaded section (228) and second threaded section (229). For example, a if first threaded section (228) and second threaded section (229) had a fine pitch, end effector (40) may articulate to more positions between the first and second articulated positions shown in FIG. 6B-6C as compared to if first threaded section (228) and second threaded section (229) had a coarse pitch. Additionally, if first threaded section (228) and second threaded section (229) had a fine pitch, end effector (40) may articulate at a slower pace per revolution of shaft assembly (226) as compared to if first threaded section (228) and second threaded section (229) had a coarse pitch.

In some versions, first threaded section (228) and second threaded section (229) may have a varying pitch to provide a progressively slowing articulation speed as end effector (40) approaches a desired articulation angle (such as the maximum articulation angle). Of course, any other suitable pitch configuration may be utilized as would be apparent to one having ordinary skill in the art in view of the teachings herein. In versions where threaded sections (228, 229) have varying pitch, it may be desirable to replace threading on threaded rings (242, 252) with pins or other features that are capable of more easily traversing a varying pitch. For instance, each ring (242, 252) may have a single pin that rides along the thread of a corresponding threaded section (228, 229). Other suitable ways of providing a varying pitch and/or other features to provide varying articulation speed will be apparent to one having ordinary skill in the art in view of the teachings herein.

In some instances, it may be desirable to include features that are configured to automatically stop motor (222) when articulation section (130) reaches a predetermined degree of articulation. By way of example only, some versions of articulation control assembly (200) may include one or more switches (e.g., reed switches) that are actuated by ring (242) or pin (244), and/or by ring (252) or pin (254), when articulation control assembly (200) reaches the state shown in FIG. 12B. Similarly, some versions of articulation control assembly (200) may include another one or more switches (e.g., reed switches) that are actuated by ring (242) or pin (244), and/or by ring (252) or pin (254), when articulation control assembly (200) reaches the state shown in FIG. 12C. In either or both cases, the one or more switches may stop motor (222) to prevent motor (222) from driving rings (242, 252) off of corresponding threaded portions (228, 229). As another merely illustrative example, an encoder or other tracking feature may be used to track rotation of drive shaft (226), and a motor controller may be used to automatically stop motor (222) when data from the encoder or other tracking feature indicates that articulation control assembly (200) has reached the state shown in FIG. 12B or the state shown in FIG. 12C. In some such versions, motor (222) comprises a stepper motor in order to provide precise stopping in response to a motor controller.

In still other versions, rings (242, 252) may be permitted to run off of corresponding threaded portions (228, 229), such that motor (222) may continue to be activated after articulation section (130) has reached a maximum articulation angle. In such versions, a spring or other biasing elements may promote re-engagement between rings (242, 252) and corresponding threaded portions (228, 229) when motor (222) is subsequently reversed.

As yet another merely illustrative example, drive shaft (226) may be fitted with a bevel gear. A driven shaft may be oriented perpendicularly to drive shaft (226). One end of the driven shaft may have a bevel gear that meshes with the bevel gear of drive shaft (226). The other end of the driven shaft may have a pinion gear that meshes with opposing racks formed at the proximal ends of translatable members (161, 162). Thus, when motor (222) is activated to rotate drive shaft (226), the meshing pinion gears will provide corresponding rotation to the driven shaft, which will in turn rotate the pinion gear. The rotating pinion gear will in turn provide opposing translation of the racks, which will in turn provide opposing longitudinal translation of translatable members (161, 162). The opposing longitudinal translation of translatable members (161, 162) will actuate articulation section (130) to deflect end effector (40) laterally from the longitudinal axis of shaft assembly (30) as described above. Thus, the bevel gears, driven shaft, pinion, and racks may serve as effective substitutes for threaded portions (228, 229) and drive members (240, 250). Other suitable drive assemblies will be apparent to those of ordinary skill in the art in view of the teachings herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus for operating on tissue, the apparatus comprising: (a) a body assembly; (b) a shaft extending distally from the body assembly, wherein the shaft defines a longitudinal axis; (c) an acoustic waveguide, wherein the waveguide comprises a flexible portion; (d) an articulation section coupled with the shaft, wherein a portion of the articulation section encompasses the flexible portion of the waveguide, wherein the articulation section further comprises: (i) a first member, and (ii) a second member, wherein the second member is longitudinally translatable relative to the first member; (e) an end effector comprising an ultrasonic blade in acoustic communication with the waveguide; and (f) an articulation control assembly comprising a motor, wherein the motor is operable to deflect the end effector away from the longitudinal axis.

Example 2

The apparatus of Example 1, wherein the articulation control assembly comprises a drive shaft, wherein the motor is operable to rotate the drive shaft.

Example 3

The apparatus of any one or more of Examples 1 through 2, wherein the articulation control assembly further comprises a first drive member connected with the first member and a second drive member connected with the second member.

Example 4

The apparatus of Example 3, wherein the first drive member is configured to convert the rotation of the drive shaft into translation of the first member and the second drive member is configured to convert rotation of the drive shaft into translation of the second member.

Example 5

The apparatus of any one or more of Examples 1 through 4, wherein the articulation control assembly is configured to drive the first member and second member of the articulation section in opposing directions simultaneously.

Example 6

The apparatus of any one or more of Examples 3 through 5, wherein the drive shaft comprises a first threaded section coupled to the first drive member and a second threaded section coupled to the second drive member, wherein the first threaded section and the second threaded section are threaded in opposing directions.

Example 7

The apparatus of any one or more of Examples 2 through 6, wherein the articulation control assembly further comprises a gear box between the motor and the drive shaft.

Example 8

The apparatus of any one or more of Examples 1 through 7, further comprising a knob configured to rotate the shaft and acoustic waveguide about the longitudinal axis relative to the body.

Example 9

The apparatus of Example 8, wherein the articulation control assembly further comprises housing, wherein the housing is fixed to the knob, wherein the motor is fixed within the housing.

Example 10

The apparatus of any one or more of Examples 1 through 9, wherein the body assembly further comprises a first switch and a second switch, wherein the first switch is operable to activate the motor to rotate a drive shaft of the motor in a first direction, wherein the second switch is operable to activate the motor to rotate the drive shaft of the motor in a second direction.

Example 11

The apparatus of Example 10, wherein the apparatus further comprises a wheel pivotally fixed to the body assembly, wherein the wheel is rotatable in a a third direction to activate the first switch, wherein the wheel is rotatable in a fourth direction to activate the second switch.

Example 12

The apparatus of any one or more of Examples 10 through 11, wherein the wheel is biased to a neutral position, wherein the wheel is configured to not activate the first switch of the second switch in the neutral position.

Example 13

The apparatus of any one or more of Examples 10 through 12, wherein the first switch and the second switch are in electrical communication with the motor via a contact and a slip ring connector.

Example 14

The apparatus of any one or more of Examples 1 through 13, wherein a distal end of the first member is configured to be longitudinally offset from a distal end of the second member when the articulation section is in aligned with the longitudinal axis.

Example 15

An apparatus for operating on tissue, the apparatus comprising: (a) a body assembly; (b) a shaft extending distally from the body assembly, wherein the shaft comprises an ultrasonic waveguide, wherein the shaft defines a longitudinal axis; (c) an articulation section coupled with the shaft; (d) an end effector coupled with the articulation section, wherein the end effector comprises an ultrasonic blade configured to engage tissue; and (e) an articulation drive assembly operable to drive articulation of the articulation section to thereby deflect the end effector from the longitudinal axis, wherein the articulation drive assembly comprises: (i) a first translating driver, (ii) a second translating driver, and (iii) a motor configured to actuate the first translating driver and the second translating driver simultaneously in opposing longitudinal directions.

Example 16

The apparatus of Example 15, wherein the articulation drive assembly further comprises a drive shaft coupling the first translating driver and the second translating driver with the motor.

Example 17

The apparatus of Example 16, wherein the first translating driver comprises a first threaded section, wherein the second translating driver comprises a second threaded section, wherein the drive shaft is operable to rotate, wherein the first translating driver is operable to translate in response to rotation of the drive shaft via the first threaded section, wherein the second translating driver is operable to translate in response to rotation of the drive shaft via the second threaded section.

Example 18

The apparatus of any one or more of Examples 15 through 17, further comprising a first band and a second band, wherein the articulation section is coupled to the first translating driver via the first band, wherein the articulation section is coupled with the second translating driver via the second band.

Example 19

An apparatus for operating on tissue, the apparatus comprising: (a) a body assembly; (b) a shaft extending distally from the body assembly, wherein the shaft defines a longitudinal axis, wherein the shaft assembly is operable to rotate about the longitudinal axis relative to the body assembly; (c) an articulation section coupled with the shaft; (d) an end effector coupled with the articulation section; (e) a first pair of translating members, wherein the first pair of translating members is operable to actuate the articulation section to thereby deflect the end effector from the longitudinal axis; and (f) a motorized drive assembly in communication with the first pair of translating members, wherein the drive assembly is configured to translate the translating members of the first pair in opposite longitudinal directions simultaneously to thereby actuate the articulation section, wherein the motorized drive assembly is operable to rotate with the shaft about the longitudinal axis relative to the body assembly.

Example 20

The apparatus of Example 19, wherein the motorized drive assembly includes a drive shaft defining a right-handed threaded section and a left-handed threaded section.

IV. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An apparatus for operating on tissue, the apparatus comprising:
   (a) a body assembly;
   (b) a shaft extending distally from the body assembly, wherein the shaft defines a longitudinal axis, wherein the shaft is configured to rotate relative to the body assembly about the longitudinal axis;
   (c) an acoustic waveguide, wherein the waveguide comprises a flexible portion;
   (d) an articulation section coupled with the shaft such that the articulation section is configured to rotate relative to the body assembly about the longitudinal axis, wherein a portion of the articulation section encompasses the flexible portion of the waveguide, wherein the articulation section further comprises:
      (i) a first member, and
      (ii) a second member, wherein the second member is longitudinally translatable relative to the first member;
   (e) an end effector comprising an ultrasonic blade in acoustic communication with the waveguide; and
   an articulation control assembly comprising:
      (i) a motor, wherein the motor is operable to electrically activate to deflect the end effector away from the longitudinal axis, wherein the motor is further configured to rotate with the shaft and articulation section relative to the body assembly about the longitudinal axis,
      (ii) a drive shaft comprising a first threaded section and a second threaded section, wherein motor is configured to rotate the drive shaft about a rotational axis, wherein the rotational axis is offset from the longitudinal axis defined by the shaft, (iii) a first drive member coupled to the first threaded section and the first member, and
(iv) a second drive member coupled to the second threading and the second member, wherein the drive shaft is configured to rotate about the rotational axis in a first rotational direction to actuate the first drive member and the second drive member in opposing directions.

2. The apparatus of claim 1 wherein the first threaded section and the second threaded section are threaded in opposing directions.

3. The apparatus of claim 1, wherein the articulation control assembly further comprises a gear box between the motor and the drive shaft.

4. The apparatus of claim 1, further comprising a knob configured to rotate the shaft and acoustic waveguide about the longitudinal axis relative to the body.

5. The apparatus of claim 4, wherein the articulation control assembly further comprises housing, wherein the housing is fixed to the knob, wherein the motor is fixed within the housing.

6. The apparatus of claim 1, wherein the body assembly further comprises a first switch and a second switch, wherein the first switch is operable to activate the motor to rotate in the first rotational direction, wherein the second switch is operable to activate the motor to rotate in a second rotational direction.

7. The apparatus of claim 6, wherein the apparatus further comprises a wheel pivotally fixed to the body assembly, wherein the wheel is rotatable in a third direction to activate the first switch, wherein the wheel is rotatable in a fourth direction to activate the second switch.

8. The apparatus of claim 6, wherein the wheel is biased to a neutral position, wherein the wheel is configured to not activate the first switch of the second switch in the neutral position.

9. The apparatus of claim 6, wherein the first switch and the second switch are in electrical communication with the motor via a contact and a slip ring connector.

10. The apparatus of claim 1, wherein a distal end of the first member is configured to be longitudinally offset from a distal end of the second member when the articulation section is in alignment with the longitudinal axis.

11. An apparatus for operating on tissue, the apparatus comprising:
(a) a body assembly;
(b) a shaft extending distally from the body assembly, wherein the shaft comprises an ultrasonic waveguide, wherein the shaft defines a longitudinal axis, wherein the shaft is configured to rotate about the longitudinal axis relative to the body assembly;
(c) an articulation section coupled with the shaft;
(d) an end effector coupled with the articulation section, wherein the end effector comprises an ultrasonic blade configured to engage tissue;
(e) an articulation drive assembly operable to drive articulation of the articulation section to thereby deflect the end effector from the longitudinal axis, wherein the articulation drive assembly is configured to rotate with the shaft about the longitudinal axis relative to the body assembly, wherein the articulation drive assembly comprises:
(i) a drive shaft extending along a second axis that is offset from the longitudinal axis, wherein the drive shaft comprises a first threaded section and a second threaded section,
(ii) a first translating driver coupled with the first threaded section of the drive shaft,
(iii) a second translating driver coupled with the second threaded section of the drive shaft,
(iv) a motor configured to rotate the drive shaft about the second axis in a first angular direction to thereby actuate the first translating driver and the second translating driver simultaneously in opposing longitudinal directions; and
(f) a user input feature electrically coupled with the motor, wherein the user input feature is operable to activate the motor.

12. The apparatus of claim 11, further comprising a first band and a second band, wherein the articulation section is coupled to the first translating driver via the first band, wherein the articulation section is coupled with the second translating driver via the second band.

13. An apparatus for operating on tissue, the apparatus comprising:
(a) a body assembly;
(b) a shaft assembly extending distally from the body assembly, wherein the shaft assembly defines a longitudinal axis, wherein the shaft assembly is operable to rotate about the longitudinal axis relative to the body assembly;
(c) an articulation section coupled with the shaft assembly;
(d) an end effector coupled with the articulation section;
(e) a first pair of translating members, wherein the first pair of translating members is operable to actuate the articulation section to thereby deflect the end effector from the longitudinal axis, wherein the pair of translating members are operable to rotate with the shaft assembly about the longitudinal axis relative to the body assembly;
(f) a motorized drive assembly comprising
(i) a motor extending along a second axis that is offset from the longitudinal axis, and
(ii) a drive shaft defining a right-handed threaded section and a left-handed threaded section, wherein the drive shaft extends along the second axis, wherein the drive shaft is in communication with the first pair of translating members, wherein the motorized drive assembly is configured to receive an electrical signal to rotate the drive shaft in a first direction to translate the translating members of the first pair in opposite longitudinal directions simultaneously to thereby actuate the articulation section, wherein the motorized drive assembly is operable to rotate with the shaft assembly about the longitudinal axis relative to the body assembly.

\* \* \* \* \*